(12) United States Patent
Huang et al.

(10) Patent No.: US 9,976,183 B2
(45) Date of Patent: May 22, 2018

(54) BIOMARKERS FOR CANCERS RESPONSIVE TO MODULATORS OF HEC1 ACTIVITY

(71) Applicant: TAIVEX THERAPEUTICS CORPORATION, Taipei (TW)

(72) Inventors: Yu-Ling Huang, Hsinchu (TW); Johnson Lau, Newport Beach, CA (US)

(73) Assignee: TAIVEX THERAPEUTICS CORPORATION, Taipei (TW)

( * ) Notice: Subject to any disclaimer, the term of this patent is extended or adjusted under 35 U.S.C. 154(b) by 232 days.

(21) Appl. No.: 13/681,253

(22) Filed: Nov. 19, 2012

(65) Prior Publication Data
US 2013/0171634 A1    Jul. 4, 2013

Related U.S. Application Data

(60) Provisional application No. 61/562,177, filed on Nov. 21, 2011.

(51) Int. Cl.
| | |
|---|---|
| *C12Q 1/68* | (2018.01) |
| *G01N 33/68* | (2006.01) |
| *G01N 33/50* | (2006.01) |
| *G01N 33/574* | (2006.01) |
| *A61K 31/337* | (2006.01) |
| *A61K 31/4439* | (2006.01) |
| *A61K 31/4745* | (2006.01) |
| *A61K 31/497* | (2006.01) |
| *A61K 31/704* | (2006.01) |
| *A61K 45/06* | (2006.01) |

(52) U.S. Cl.
CPC .......... *C12Q 1/6886* (2013.01); *A61K 31/337* (2013.01); *A61K 31/4439* (2013.01); *A61K 31/4745* (2013.01); *A61K 31/497* (2013.01); *A61K 31/704* (2013.01); *A61K 45/06* (2013.01); *G01N 33/5017* (2013.01); *G01N 33/574* (2013.01); *G01N 33/6893* (2013.01); *G01N 2800/52* (2013.01)

(58) Field of Classification Search
None
See application file for complete search history.

(56) References Cited

U.S. PATENT DOCUMENTS

| | | |
|---|---|---|
| 2006/0140956 A1 | 6/2006 | Lee et al. |
| 2011/0071032 A1 | 3/2011 | Zellinger et al. |
| 2011/0230486 A1 | 9/2011 | Lau et al. |

FOREIGN PATENT DOCUMENTS

| | | |
|---|---|---|
| WO | 2005/026137 | 3/2005 |
| WO | 2007/004038 | 1/2007 |
| WO | 2009/140621 | 11/2009 |
| WO | 2010/056506 | 5/2010 |
| WO | 2011/115998 | 9/2011 |

OTHER PUBLICATIONS

Duffy, M. et al., "A Personalized Approach to Cancer Treatment: How Biomarkers Can Help", Clinical Chemistry, vol. 54, No. 11, pp. 1770-1779, 2008.
Patent Cooperation Treaty, "International Preliminary Report on Patentability", dated Sep. 18, 2012.
Patent Cooperation Treaty, "International Search Report and Written Opinion", PCT/2011/028532, dated 7, Nov. 2011.
Qiu, X-L et al., "Synthesis and Biological Evaluation of a Series of Novel Inhibitor of Nek2/Hec1 Analogues", Journal of Medical Chemistry, vol. 52, No. 6, pp. 1757-1767, Mar. 26, 2009.
Wu, G. et al., "Small Molecule Targeting the Hec/Nek2 Mitotic Pathway Suppresses Tumor Cell Growth in Culture and in Animal", Cancer Research, vol. 68, pp. 8393-8399, 2008, published online Oct. 15, 2008.
Chan, H.S. et al., "Multidrug Resistance Protein (MRP) Expression in Retinoblastoma Correlates with the Rare Failure of Chemotherapy despite Cyclosporine for Reversal of P-Glycoprotein", Cancer Research, 1997, vol. 57, pp. 2325-2330.
Ferretti, C. et al., "Expression of the kinetochore protein Hec1 during the cell cycle in normal and cancer cells and its regulation by the pRb pathway", Cell Cycle, 2010, vol. 9, No. 20, pp. 4174-4182.
Patent Cooperation Treaty, "Notification of Transmittal of the International Search Report and Written Opinion of the International Searching Authority, or the Declaration", PCT Application No. PCT/US12/65923, dated Feb. 11, 2013.
PubChem, "F5773-1986—Compound Summary", http://pubchem.ncbi.nl.m.nih.gov/summary/summary.cgi?cid=4551765#x304, Feb. 2, 2013.
PubChem, "F5773-1987—Compound Summary", http://pubchem.ncbi.nl.m.nih.gov/summary/summary.cgi?cid=4551766#x304, Feb. 2, 2013.
PubChem, "F5773-1988—Compound Summary", http://pubchem.ncbi.nl.m.nih.gov/summary/summary.cgi?cid=4551767#x304, Feb. 2, 2013.
Sahu, M. et al., "Condensed Heterocycles: Synthesis of 2-Aryl-5-oxo-5-H-pyrido-[3',2': 5,6]pyrimido[2,1-h][1,3,4]-oxadiazoles/thiadiazoles, 9-Aryl-5-oxo-5H-pyrido[3',2': 5,6]pyrimido[2, 1-h]-thiadiazoles & 2-Aryl-6-hydroxy[1,3,4]-thiadiazolo/thiazolo[3,2-1]-benzimidazoles", Indiana Journal of Chemistry, Dec. 1986, vol. 25B, pp. 1266-1268.
PubChem, "ZINC00946516—Compound Summary", http://pubchem.ncbi.nl.m.nih.gov/summary/summary.cgi?cid=1185425#x304, Feb. 2, 2013.
PubChem, "ZINC01746105—Compound Summary", http://pubchem.ncbi.nl.m.nih.gov/summary/summary.cgi?cid=155416#x304, Feb. 2, 2013.
PubChem, "ZINC04072672—Compound Summary", http://pubchem.ncbi.nl.m.nih.gov/summary/summary.cgi?cid=4168446#x304, Feb. 2, 2013.

*Primary Examiner* — Jehanne S Sitton
(74) *Attorney, Agent, or Firm* — Lewis Roca Rothgerber Christie LLP

(57) ABSTRACT

Contemplated compositions and methods are drawn to biomarkers and methods related to treatment of neoplastic disease with Hec1 inhibitor. Gene status and/or expression levels of Hec1(HEC), Rb(RB1), and/or p53 (TP53) may be useful as biomarkers for sensitivity to treatment with a Hec1 inhibitor. In addition, Hec 1 inhibitors may show synergistic effects when used in conjunction with cytotoxic drugs.

8 Claims, 11 Drawing Sheets

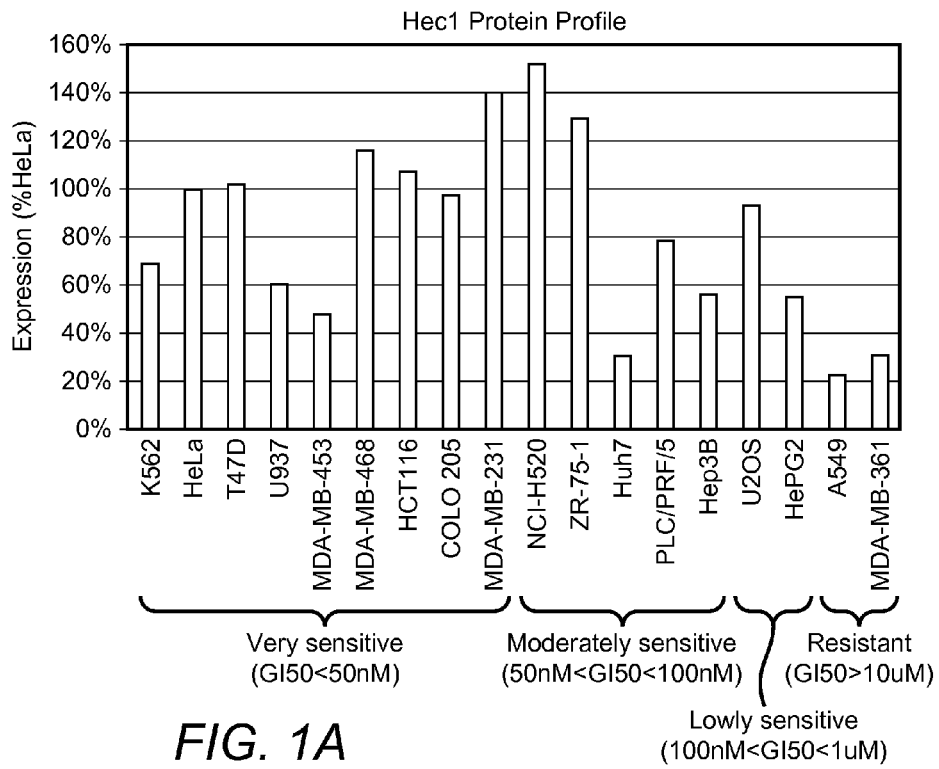
FIG. 1A
FIG. 1B
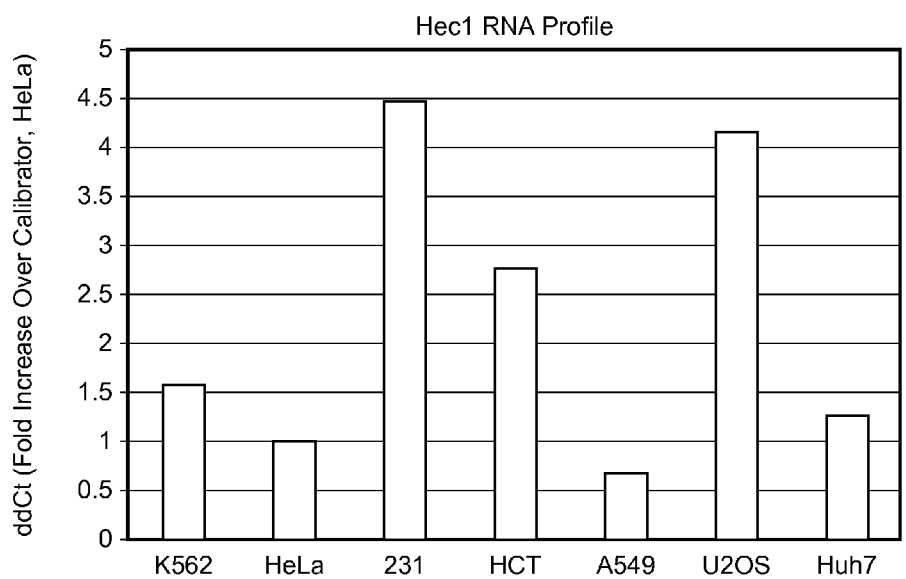

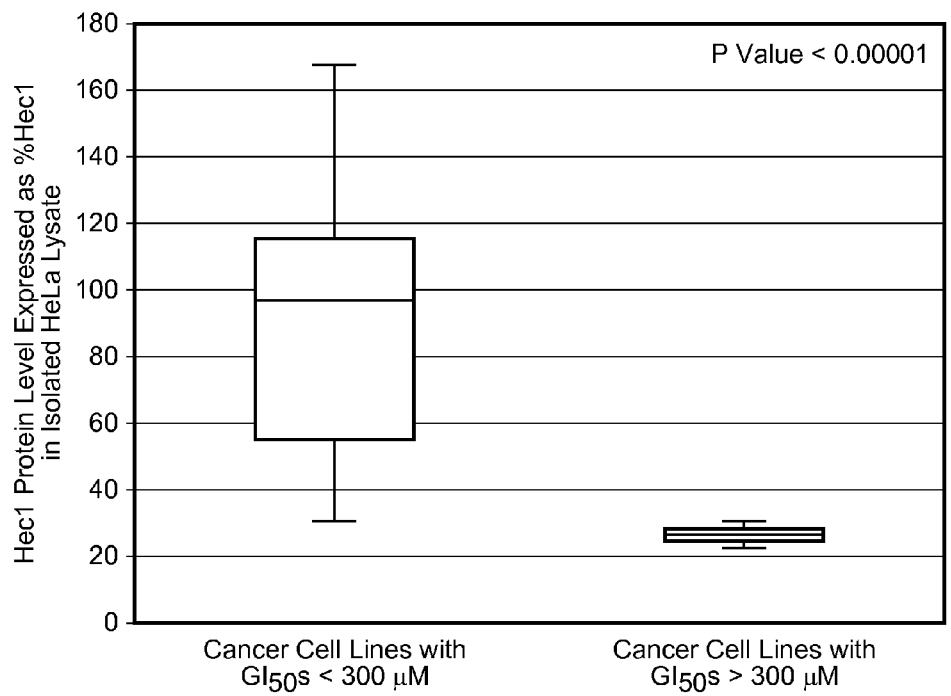
FIG. 1C
FIG. 1E
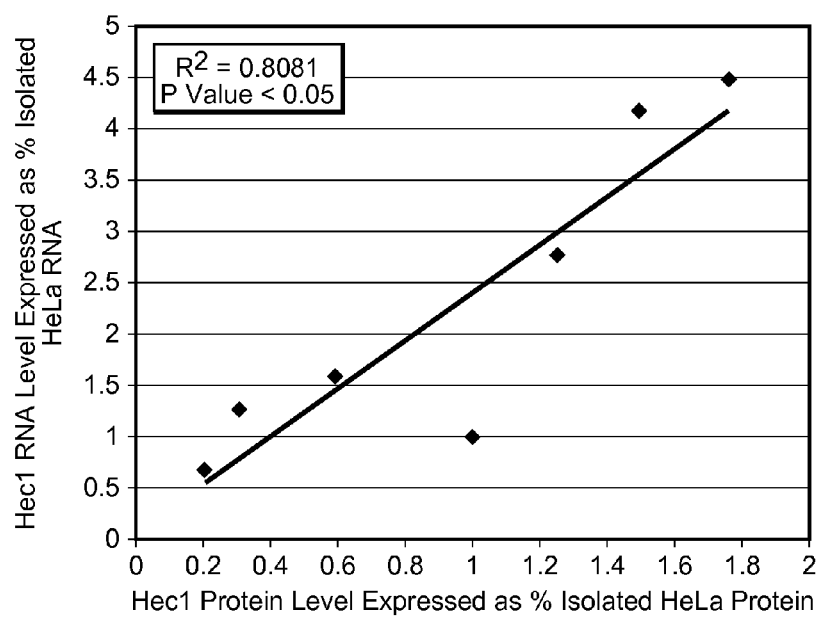

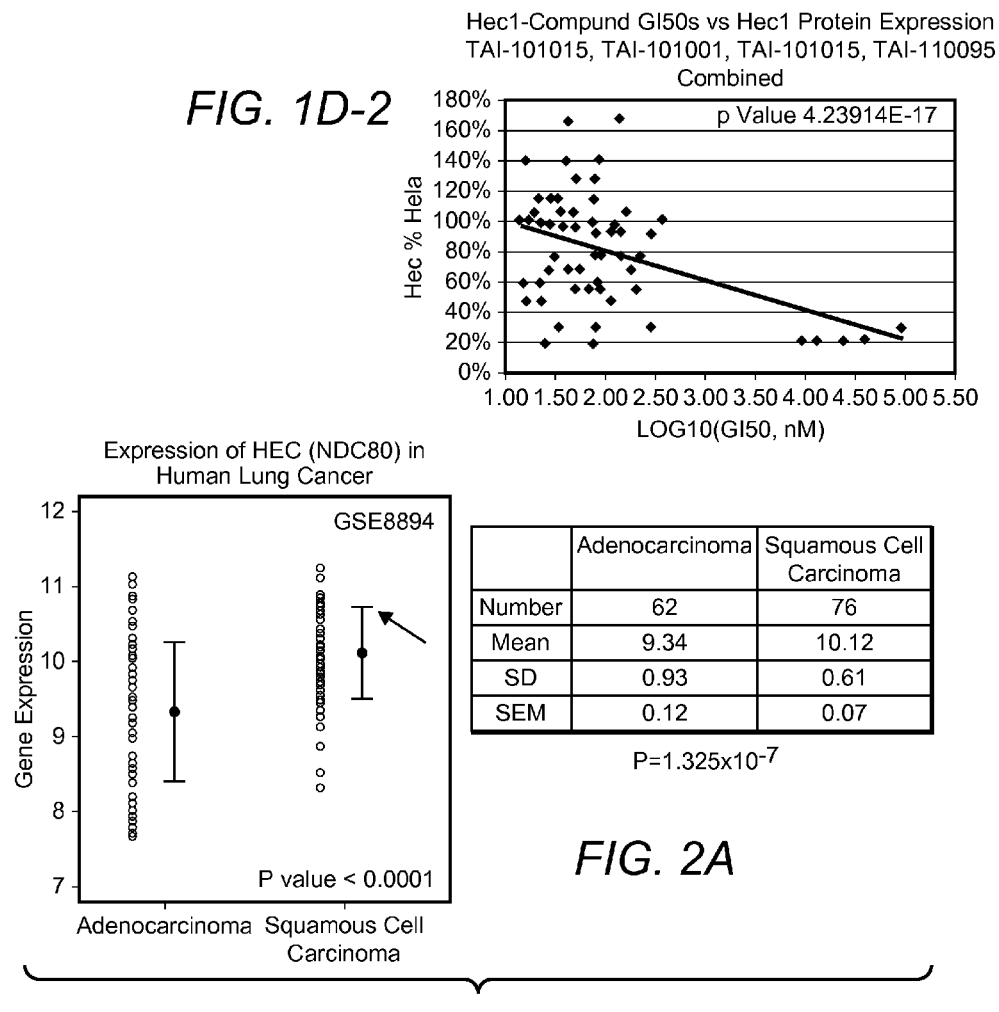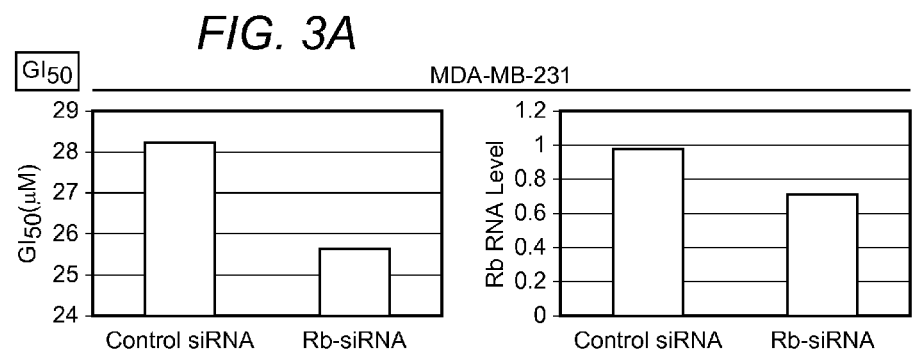

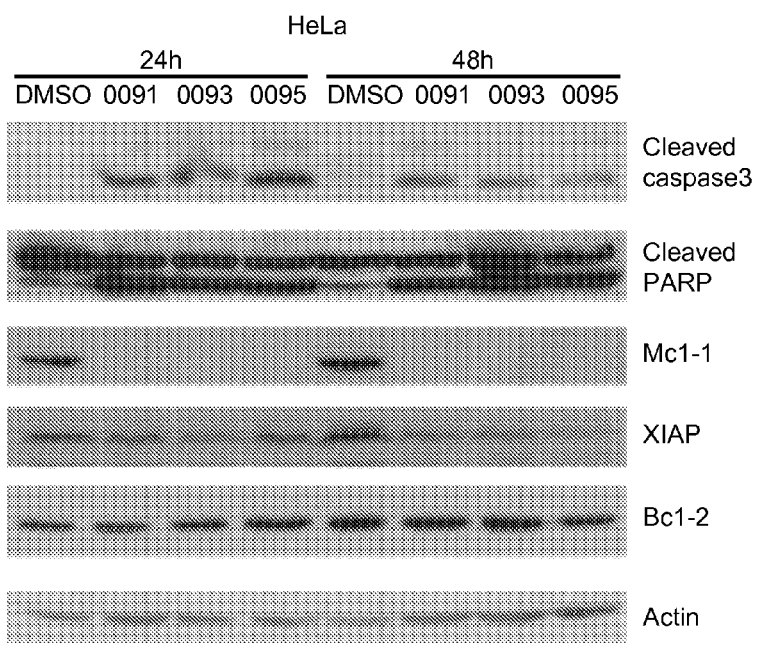
FIG. 5B
FIG. 5C
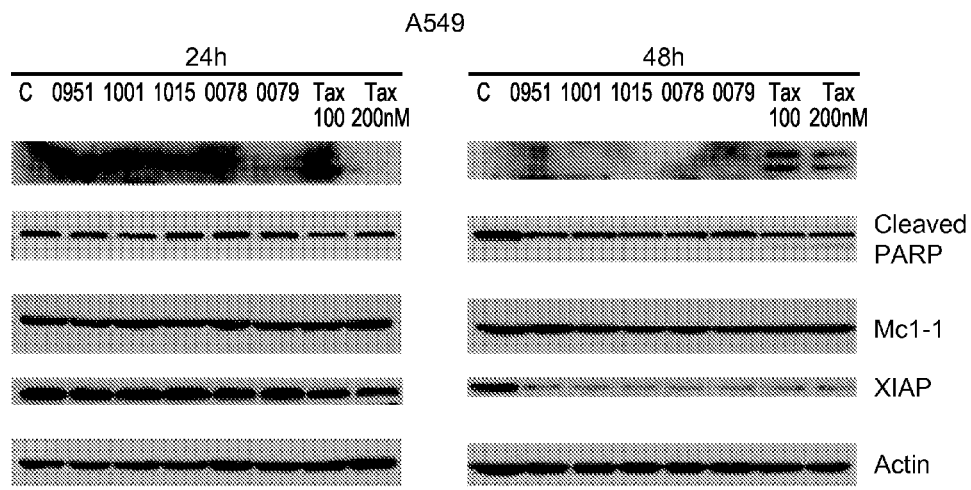

SEQUENCE LISTING

<160> NUMBER OF SEQ ID NOS: 6

<210> SEQ ID NO 1
<211> LENGTH: 26
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(26)
<223> OTHER INFORMATION: GAPDH forward primer

<400> SEQUENCE: 1
ggtttacatg ttccaatatg attcca                                          26

<210> SEQ ID NO 2
<211> LENGTH: 23
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(23)
<223> OTHER INFORMATION: GAPDH reverse primer

<400> SEQUENCE: 2
atgggatttc cattgatgac aag                                             23

<210> SEQ ID NO 3
<211> LENGTH: 20

```
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(20)
<223> OTHER INFORMATION: Rb forward primer

<400> SEQUENCE: 3
gcagtatgct tccaccaggc                                          20

<210> SEQ ID NO 4
<211> LENGTH: 21
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(21)
<223> OTHER INFORMATION: RB reverse primer

<400> SEQUENCE: 4
aagggcttcg aggaatgtga g                                        21

<210> SEQ ID NO 5
<211> LENGTH: 17
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(17)
<223> OTHER INFORMATION: p53 forward primer

<400> SEQUENCE: 5
gcccccaggg agcacta                                             17

<210> SEQ ID NO 6
<211> LENGTH: 19
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(19)
<223> OTHER INFORMATION: p53 reverse primer

<400> SEQUENCE: 6
gggagaggag ctggtgttg                                           19
```

BIOMARKERS FOR CANCERS RESPONSIVE TO MODULATORS OF HEC1 ACTIVITY

This application claims priority to U.S. provisional application with the Ser. No. 61/562,177, filed 21 Nov. 2011.

FIELD OF THE INVENTION

The field of the invention is identification and use of biomarkers for determining the sensitivity of proliferative diseases to molecularly targeted therapeutic agents, and in particular HEC1 inhibitors in combination with a cytotoxic agent.

BACKGROUND OF THE INVENTION

Over 1.6 million new cancer diagnoses and about 580,000 deaths from cancer are expected to occur in the United States in 2012. Cancer is currently the second most common cause of death in the US, trailing behind the leading cause, heart disease. Although various new cancer treatments have been developed over the past decade, the five-year relative survival rate for all cancers diagnosed between 1999 and 2006 is 68%, with estimated deaths of 28% and 26% for lung cancer in males and females, respectively, 15% for breast cancer in females, and 11% for prostate cancer. Such statistics reflect a critical need for further advances in available treatments.

Personalized medicine has revolutionized the trial and error process of current medical treatment and improved patient response rates by utilizing biomarker profiles to more effectively predict a patient's response to a drug and to reduce the time spent in ineffective treatment that permits disease to advance. At least in certain cases such an approach has allowed for a more targeted and thus more effective treatment, highlighting the potential benefit of use of biomarkers in customizing patient treatment regimens to increase therapy success rates.

For example, at the 47th Annual Meeting of the American Society of Clinical Oncology (June, 2011), Tsimberidou et at from the MD Anderson Cancer Center presented a study describing the success of treatment regimens targeting PIK3CA, mTOR, BRAF, MEK, multikinases, KIT or EGFR in 175 patients with one genetic aberration. This study showed that the response rate was 27% with matched targeted therapy versus 5% observed for patients treated with non-matched therapy. Other markers with at least some success for improvement in treatment outcome for use in personalized medicine were described by Duffy and Crown (Clinical Chemistry, 2008, 54(11):1770-1779). This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Faulty chromosomal segregation and uncontrolled mitotic proliferation are hallmarks of neoplastic disease. However, despite the availability of an increasing number of cancer markers, there remains a lack for markers indicative of susceptibility to drugs that target spindle and kinetochore regulation or mitotic checkpoint control. Hec1, for example, is a critical component in spindle checkpoint signaling that is highly expressed in cancer and helps assure correct segregation of chromosomes during cell division. Several potentially powerful Hec1 inhibitors have recently been reported (see e.g., WO 2011/115998 to Lau and Huang; Qiu et at in J. Med. Chem., 2009, 52(6):1757-1767; Wu et at in Cancer Res., 2008 Oct. 15, 68(20):8393-9). While at least some of the compounds have shown promising results, there is, however, no guidance as to any biomarkers that would be indicative of increased treatment success with such compounds.

Thus, there is still a need for biomarkers for cancers responsive to modulators of Hec1 activity.

SUMMARY OF THE INVENTION

The inventive subject matter is drawn to biomarkers and methods related to treatment of neoplastic diseases, where the disease is treated with a Hec1 inhibitor. More specifically, the inventors have now discovered that the status and/or expression level of Hec1(HEC), Rb(RB1), and/or p53 (TP53) can be used as predictive biomarkers for treatment of various disease states where the disease is treated with a Hec1 inhibitor, where the status is with respect to wild-type versus mutant genotype and/or deficient/absent gene expression.

Therefore, in one embodiment of the inventive subject matter, identification of biomarker profiles is used to determine sensitivity of proliferative diseases such as cancer to Hec1 inhibitors or otherwise Hec1 targeting compounds. Therefore, a method of determining the sensitivity of a proliferative disease and/or a neoplastic cell in a subject to treatment with a Hec1 inhibitor is contemplated that includes a step of determining status and/or expression levels of one or more of Hec1(HEC), Rb(RB1), and p53 (TP53) in a sample derived from the subject. Such determination may include forming a detectable complex that provides a test result. In some embodiments the test result may be compared to reference result related to a status and/or expression levels of one or more of Hec1(HEC), Rb(RB1), and p53 (TP53).

In another embodiment of the inventive concept a method of selecting a subject and/or evaluating a patient suffering from a proliferative or neoplastic disease for treatment with a Hec1 inhibitor is contemplated that includes a step of determining status and/or expression levels of one or more of Hec1(HEC), Rb(RB1), and p53 (TP53) in a sample derived from the subject. Such determination may include forming a detectable complex, and can provide a test result. In some embodiments the test result may be compared to a reference result related to a status and/or expression levels of one or more of Hec1(HEC), Rb(RB1), and p53 (TP53) obtained from a reference cell to determine sensitivity. Such sensitivity may be used to provide an evaluation or selection result.

In some embodiments of the inventive concept, expression levels of Hec1 may be determined; in such embodiments an increased expression level may be indicative of sensitivity of a neoplastic or proliferative cell to a Hec1 inhibitor. In other embodiments of the inventive concept the status of at least one of Rb and p53 may be determined; in such embodiments deletion of Rb and/or p53 or presence of a mutated Rb and/or p53 may indicate sensitivity of a neoplastic or proliferative cell to a Hec1 inhibitor. Hec1, Rb, and/or p53 status and/or expression may be characterized by quantification of nucleic acids encoding for Hec1, Rb, and/or p53, by sequencing of nucleic acids encoding for Hec1, Rb, and/or p53, by hybridization of nucleic acids encoding for Hec1, Rb, and/or p53, or by a combination of these. Alternatively, Hec1, Rb, or p53 status and/or expression may be characterized by quantification and/or sequence characterization of Hec1 protein, Rb protein, and p53 protein. In some embodiments of the inventive concept, both nucleic acid and protein related to Hec1, Rb, and/or p53 may be characterized.

In yet another embodiment of the inventive subject matter, a method of a patient suffering from a neoplastic disease for treatment with a Hec1 inhibitor is contemplated that includes a step of determining a molecular type of the neoplastic disease from a sample derived from the subject and determining for the molecular type an expression level of at least one of Hec1, Rb, and p53. Such determination may include forming a detectable complex, and can provide an evaluation result. In such an embodiment an increased level of Hec1 expression and/or deletion or the presence of a mutated form of Rb and/or p53 relative to a corresponding reference value or result may be indicative of the suitability of the patient's neoplastic disease with a Hec1 inhibitor. Neoplastic diseases of such an embodiment include, but are not limited to, breast cancer, lung cancer, colon cancer, and liver cancer.

Another embodiment of the inventive subject matter is a method for treating a neoplastic cell that is sensitive to a Hec1 inhibitor by contacting the neoplastic cell with a Hec1 inhibitor and a second chemotherapeutic/cytotoxic agent. Such method may utilize a dosage or dosages that is/are effective in achieving a synergistic result on growth inhibition of such a neoplastic cell. Suitable Hec1 inhibitors include, but are not limited to, N-(4-(4-isopropoxy-2,6-dimethylphenyl)thiazol-2-yl)isonicotinamide (100951); N-(4-(4-(4-methoxyphenoxy)-2,6-dimethylphenyl)thiazol-2-yl)isonicotinamide (101001); 2-fluoro-N-(4-(4-(4-methoxyphenoxy)-2,6-dimethylphenyl)thiazol-2-yl)isonicotinamide (101015); N-(4-(4-(5-(2-methoxyethoxy)pyrazin-2-yloxy)-2,6-dimethylphenyl)thiazol-2-yl)isonicotinamide (Hec110091); N-(4-(4-(5-(2-methoxyethoxy)pyrazin-2-ylthio)-2,6-dimethylphenyl)thiazol-2-yl)isonicotinamide (110095); and N-(4-(4-(5-(2-(dimethylamino)ethoxy)pyrazin-2-ylthio)-2,6-dimethylphenyl)thiazol-2-yl)isonicotinamide. Such Hec1 inhibitors may be the form of free bases or in the form of salts. Such an embodiment may utilize cytotoxic and/or chemotherapeutic drugs such as taxol, doxorubicin, and topotecan, however use of any suitable cytotoxic and/or chemotherapeutic drug or drugs is contemplated.

Yet another embodiment of the inventive subject matter is a method for treating a neoplastic cell that is multi-drug resistant (or resistant to treatment with imatinib) by contacting the neoplastic cell with a Hec1 inhibitor at a dose effective to achieve growth inhibition. In some embodiments of the inventive concept the Hec1 inhibitor may be used in combination with a second chemotherapeutic or cytotoxic agent. Suitable Hec1 inhibitors include, but are not limited to, N-(4-(4-isopropoxy-2,6-dimethylphenyl)thiazol-2-yl)isonicotinamide (100951); N-(4-(4-(4-methoxyphenoxy)-2,6-dimethylphenyl)thiazol-2-yl)isonicotinamide (101001); 2-fluoro-N-(4-(4-(4-methoxyphenoxy)-2,6-dimethylphenyl)thiazol-2-yl)isonicotinamide (101015); N-(4-(4-(5-(2-methoxyethoxy)pyrazin-2-yloxy)-2,6-dimethylphenyl)thiazol-2-yl)isonicotinamide (Hec110091); N-(4-(4-(5-(2-methoxyethoxy)pyrazin-2-ylthio)-2,6-dimethylphenyl)thiazol-2-yl)isonicotinamide (110095); and N-(4-(4-(5-(2-(dimethylamino)ethoxy)pyrazin-2-ylthio)-2,6-dimethylphenyl)thiazol-2-yl)isonicotinamide. Such Hec1 inhibitors may be the form of free bases or in the form of salts. Such an embodiment may utilize cytotoxic and/or chemotherapeutic drugs such as taxol, doxorubicin, and topotecan, however use of any suitable cytotoxic and/or chemotherapeutic drug or drugs is contemplated.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A shows Hec1 protein expression levels in total protein from asynchronously maintained cell lines. Hec1 protein expression levels were quantitated and expressed in % relative to HeLa expression levels and categorized as very sensitive (GI50<50 nM), moderately sensitive (50 nm<GI50<100 nm), partially sensitive (100 nm<GI50<10 μM), or resistant (with GI50>10 μM to a Hec1 inhibitor. FIG. 1B shows Hec1 RNA expression levels in total RNA. Hec1 RNA expression was quantitated, expressed in % relative to HeLa expression levels, and graphed against protein expression for correlation. FIG. 1C shows compiled data for Hec1 protein expression in cancer cell lines categorized as sensitive (GI50<300 μM) or resistant (GI50>300 μM) in response to a different Hec1 inhibitor. FIG. 1E shows the correlation between Hec1 RNA expression level in terms of % total RNA and Hec1 protein expression level in terms of % total protein.

FIG. 2 shows Hec1 expression in different cancer cell lines and in subtypes of lung cancer and breast cancer from human patient samples. FIG. 2A and FIG. 2B show Hec1 (NDC80) expression data obtained from GEO database GSE8894 and GSE14814, respectively, for human lung cancer tumor expressed as the logarithm of expression intensity; results show high Hec1 expression in squamous cell carcinoma.

FIG. 3 shows the effect of siRNA knockdown of Rb on cancer cell sensitivity to Hec1 inhibitory compounds. FIG. 3A shows the effect of knockdown by transfection of wild-type Rb MDA-MB-231 cells transfected with either control siRNA or siRNA targeting Rb (siRb) on sensitivity (in terms of GI50) to Hec1 inhibitory compound 101001. Rb RNA expression in transfected cells is also shown.

FIG. 4 shows the effect of siRNA knockdown of p53 on cancer cell sensitivity to Hec1 inhibitory compounds.

Figure 4A:
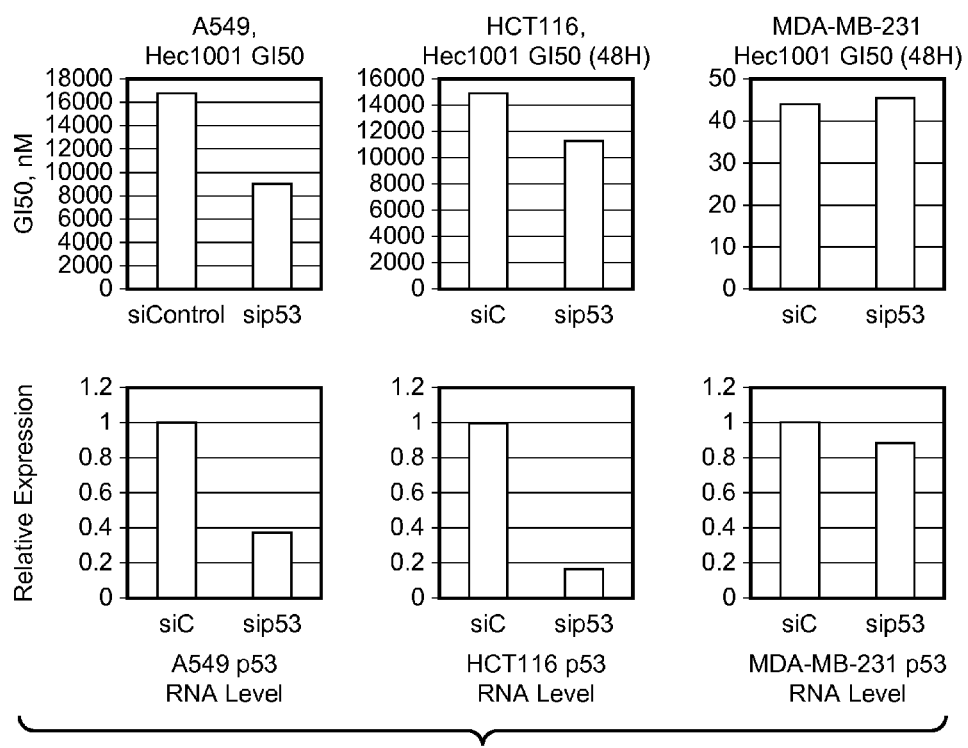
FIG. 4A shows the effect of knockdown by transfection of wild-type wild-type p53 cells (A549, HCT116) transfected either control siRNA or siRNA targeting p53 (sip53) on sensitivity (in terms of GI50) to Hec1 inhibitory compound 101001. Cellular sensitivity is expressed in GI50(nM). Expression of p53 RNA from transfected cells is also shown.

(HeLa) transfected with one of two different siRNAs directed to p53 and treated as in FIG. 4A, expressed as percent growth inhibition relative to non-drug-treated cells. Immunoblots of lysates from transfected cells probed for p53 are shown below the corresponding inhibition graphs.

Figure 5A:
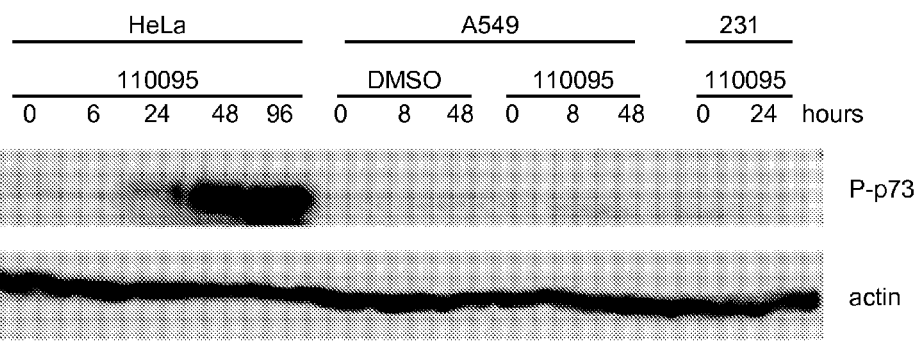
Figure 5D:
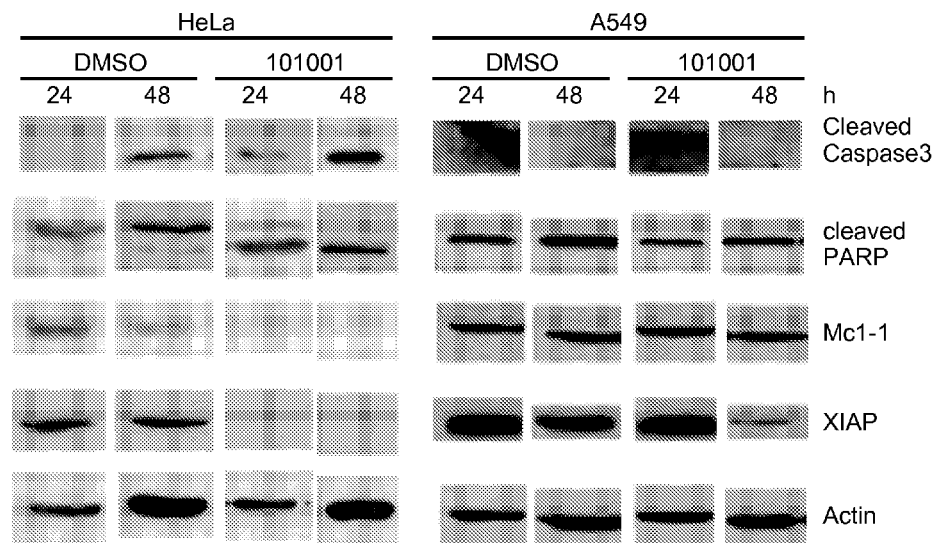

FIG. 5 shows differences in induction of phosphorylation of p73, activation of apoptotic markers, and downregulation of anti-apoptotic markers by Hec1 inhibitor between drug-responsive cells (GI50<10 uM) and non-drug-responsive cells (GI50>10 uM). Actin is also shown as a control. FIG. 5A shows an immunoblot that demonstrates the effect of Hec1 inhibitory compounds (200 nM) phosphorylated p73 (P-p73) expression in drug-responsive HeLa cells and non-drug-responsive A549 cells treated with select Hec1 inhibitory compounds at 200 nM at various time points. FIG. 5B shows an immunoblot demonstrating the effect of Hec1 inhibitory compounds (1 µM) on the expression of apoptotic markers caspase3, PARP and anti-apoptotic markers Mcl-1, XIAP, Bcl-2 in drug-responsive HeLa cells. FIG. 5C shows an immunoblot demonstrating the effect of select Hec1 inhibitory compounds and Taxol on the expression of apoptotic markers caspase3, PARP and anti-apoptotic markers Mcl-1, XIAP, Bcl-2 in non-drug-responsive A549 cells. FIG. 5D shows an immunoblot demonstrating the effect of Hec1 inhibitory compound 101001 on the expression of apoptotic markers caspase3, PARP and anti-apoptotic markers Mcl-1, XIAP, Bcl-2 in drug-responsive HeLa and non-drug-responsive A549 cells.

Figure 6B:
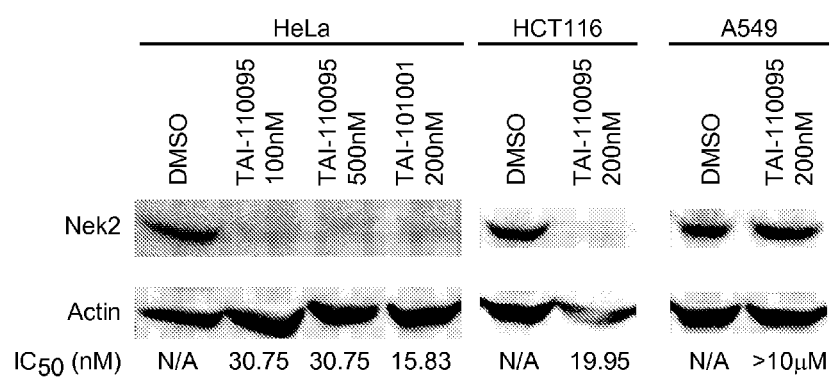
Figure 6A:
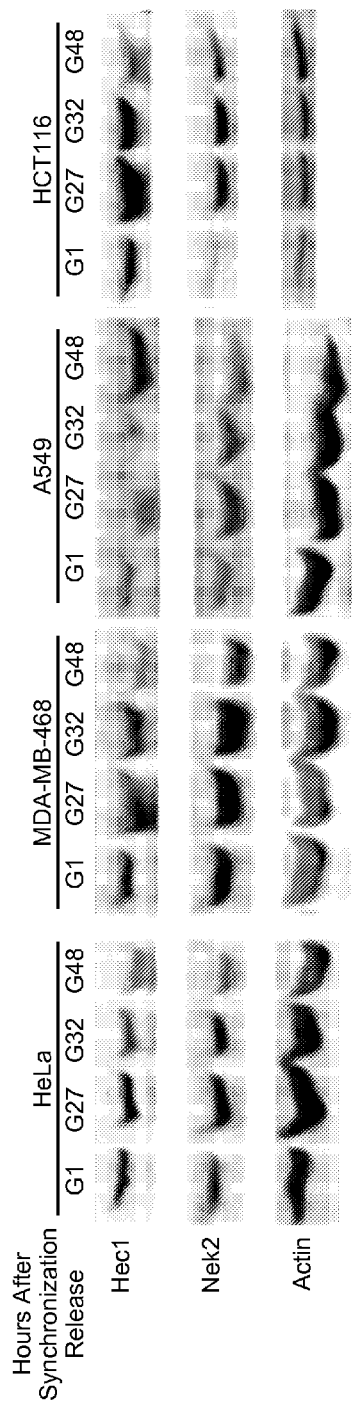
Figure 6C:
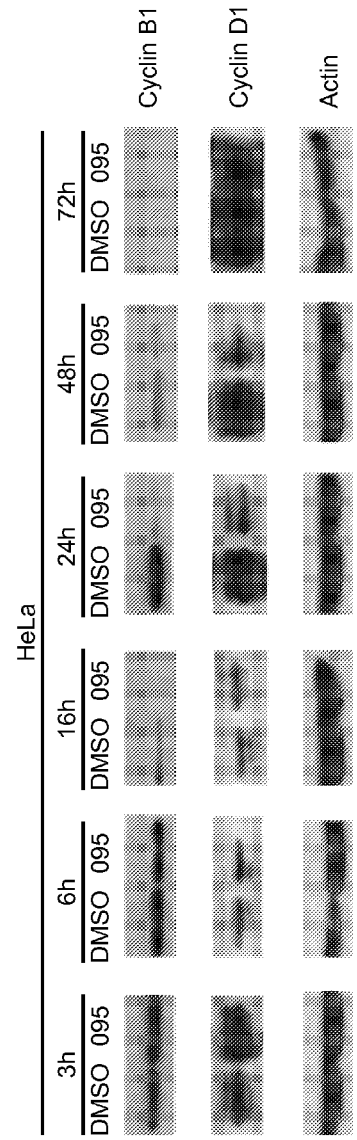

FIG. 6 shows differential cell cycle regulation of Hec1 and Nek2 protein expression and differential down-regulation of Nek2 protein by Hec1 inhibitor in drug-responsive cells (GI50 10 µM) and non-drug-responsive cells (GI50>10 µM). FIG. 6A shows immunoblots of Hec1 and Nek2 from synchronized drug-responsive cells (HeLa, MDA-MB-468, HCT116) and non-drug-responsive cells (A549) at various time points. Actin is included as a loading control. FIG. 6B shows immunoblots of Nek2 from drug-responsive cells (HeLa, HCT116) and non-drug-responsive cells (A549) treated with a DMSO control and with a Hec1 inhibitory compound at different concentrations. FIG. 6C shows immunoblots of cyclin B1 and cyclin D1 for HeLa cells treated with either a DMSO control or a Hec1 inhibitory compound for different periods of time. Actin is included as loading control.

The embodiments set forth in the drawings are illustrative in nature and are not intended to be limiting of the invention defined by the claims. Moreover, individual features of the drawings and the invention will be more fully apparent in view of the detailed description.

DETAILED DESCRIPTION

Based on the recent discovery of a small molecule that was able to selectively and/or specifically target the Hec1/Nek2 pathway, the inventors have developed various improved Hec1 inhibitors that target the kinetochore component Hec1, which is overexpressed in various human cancers. These compounds led the inventors to investigate the roles of Hec1, Rb and p53 in Hec1 inhibitor drug sensitivity in cancer cells.

Cells rely on well-regulated cell cycle control throughout mitosis to function properly. The deregulated mitotic processes observed in cancer cells involve processes such as aberrant spindle formation and chromosome segregation. Hec1 is expressed most abundantly in rapidly dividing cells, but not in terminally differentiated cells. Hec1 has been shown to be upregulated in brain, liver, breast, and lung tumor cells in genome-wide expression profiles, overexpressed in cervical, colorectal, breast cancer, and lung cancer cell lines, and colorectal and gastric cancer tissues. Thus differential expression of Hec1 in rapidly differentiated cells, transformed cell lines, and cancerous tissues suggest that Hec1 may be an excellent candidate in targeted therapy of human cancers. Similarly, the potential of Hec1 as a target for cancer therapy can be supported by statistical analysis correlating Hec1 expression and IC50.

Hec1 is associated with the retinoblastoma gene (Rb), which plays a significant role in the G2-M phase of the cell cycle. More specifically, in the G2-M phase Rb interacts with protein phosphatase 1 alpha, a protein shown to be essential for kinetochore function. Phosphorylation of Rb in G1-S phases of the cell cycle is coordinated with the induction and degradation of cyclins in the G2-M phase. Rb also regulates chromosome segregation directly and interacts with Hec1 at G2-M phase. Cells lacking functional Rb cannot finish mitosis properly and mitosis of such cells results in hyperploidy. These relationships suggest that Rb may have a role in the mitotic steps involving Hec1.

P53 is a multifunctional protein that includes various structural domains that are involved in specific, complex interactions with DNA, RNA, protein and cell metabolites. The p53 gene is often mutated in cancer, primarily with missense mutations resulting in single amino acid residue replacements). Such mutated p53 proteins are grouped into different structural groups. For example, p53 proteins with "hotspot" mutations occurring within the DNA binding domain can be characterized as DNA contact mutants or conformational mutants. Mutant p53 is often highly expressed throughout tumor progression (including advanced and distant metastases), implying that it may possess gain-of-function (GOF) properties. Such GOF properties allow mutant p53 to interact with sites on the chromatin that differ from chromatin sites that interact with wild type p53, and with a variety of transcriptional factors that may up-regulate or repress genes such as multi-drug resistance 1 gene or caspase-3, respectively. Inactivation of the wild type p53 has also been shown to enhance sensitivity to multiple chemotherapeutic agents including cisplatin, carboplatin, and taxol.

Based on the above considerations and other factors, the inventors have now discovered that sensitivity of cells to Hec1 inhibitors can be accurately and reliably predicted by the status and/or expression level of Hec1(HEC), Rb(RB1), and/or p53 (TP53). This advantageously permits early identification of cancer patients that may benefit from Hec1 inhibitor therapy, which in turn may lead to more effective treatment of their disease while it is still in an early stage.

More specifically, the inventors have discovered that the Hec1 expression level is positively correlated with sensitivity of neoplastic cells to treatment with Hec1 inhibitors, and that deletion, dysregulation, or dysfunction of Rb and/or p53 are also positively correlated with sensitivity of neoplastic cells to treatment with Hec1 inhibitors. It should therefore be appreciated that such correlation may not only allow prediction of treatment success of neoplastic cells and tissue with Hec1 inhibitors, but also that certain cancer types will be a priori susceptible or, alternatively, resistant to treatment with Hec1 inhibitors.

For example, as is also further shown in more detail below, certain neoplastic cells lines and neoplastic cells with relatively high expression of Hec1 (e.g., Hep3B/hepatocellular carcinoma, HeLa/cervical cancer, T47D/metastatic, pleural, invasive, ductal carcinoma) may be highly susceptible to treatment with Hec1 inhibitors, whereas other cells lines with substantially low or no Hec1 expression (e.g., MOLT-4/acute lymphoblastic leukemia, N87/gastric cancer) may be significantly less sensitive (or resistant) to treatment with Hec1 inhibitors.

Such differential sensitivity may also be useful in the typing and/or treatment of single types or categories of cancer. For example, molecular sub-types of breast cancer are categorized into types I-VI, however only types I and IV exhibit significant levels of Hec1 expression and are thus likely to be sensitive to Hec1 inhibitor treatment. Similarly, identification of a specified type or category of a cancer in a patient may indicate likely sensitivity to Hec1 inhibitors, and therefore may be utilized to optimize treatment.

Thus, one embodiment of the inventive concept is a method of selecting subjects suffering from a proliferative disease for treatment with a Hec1 inhibitor (optionally in combination with a cytotoxic agent), wherein such selection is based on prior determination of Hec1 expression and/or status. In one especially preferred aspect of the inventive subject matter, Hec1 expression and/or status is determined by quantification of the level of expression of the wild type Hec1 (HEC) gene, presence of a mutated Hec1 (HEC) gene, or by determination of absence, deficiency (relative to a healthy control) or deletion of the Hec1(HEC) gene. Similarly, it should also be appreciated that such quantification may also include a determination of the level of expression and/or post-translational modification(s) of Hec1 in a sample obtained from the subject. For example, such determination may be performed by determining a level of expression of wild type Hec1 in the subject and comparing it to a level of expression of wild type Hec1 (HEC) gene in a healthy control subject. Additionally, or alternatively, a control subject may also represent a tumor responsive or non-responsive that is responsive to a specific therapy—most typically treatment with a Hec1 inhibitor. In such a case, where the control represents a tumor responsive to the therapy, a higher expression of wild type Hec1 (HEC) gene in the individual as compared with the control may predict likely responsiveness to the therapy. Conversely, where a control represents a tumor resistant to the therapy, a lower level of expression of Hec1 in the individual as compared with the control may predict likely resistance to the therapy.

Another embodiment of the inventive subject matter (and particularly, but not necessarily, in subjects with high Hec1 (HEC) expression levels relative to a control), a method is contemplated in which patients are selected for treatment with a Hec1 inhibitor where the patient suffers from a proliferative disease suitable for treatment with a Hec1 inhibitor, and wherein such patient selection relies (at least in part) on a step of characterizing or determining Rb status. Rb status may be characterized by determining the presence of the wild type Rb (RB1) gene, the presence of a mutated Rb (RB1) gene, the absence, deficiency, or deletion of the Rb (RB1) gene, and/or the level of expression and/or post-translational modification(s) of Rb in a sample derived from the subject. As noted above, it should be appreciated that reduced or lacking expression of Rb, or having a dysregulated and/or dysfunctional Rb (RB1), may be indicative of responsiveness of a neoplastic cell to treatment with a Hec1 inhibitor. Thus, a patient population for treatment with a Hec1 inhibitor may be selected on the basis of subjects showing insufficient/mutated/deleted Rb (RB1) status.

Similarly, and in yet another embodiment of the inventive concept, a method of selecting subjects suffering from a proliferative disease for treatment with a Hec1 inhibitor (optionally in combination with a cytotoxic agent) is contemplated, wherein such method includes a step of determining the sensitivity of the proliferative disease in said subjects to treatment using a Hec1 inhibitor is determined by characterizing or determining p53 status. For example, such methods may comprise a step of determining p53 status via identification and/or quantification of the wild type p53 (TP53) gene, a mutated p53 (TP53) gene, or the absence, deficiency of deletion of the p53 (TP53) gene and/or the level of expression and/or post-translational modification(s) of p53 in a sample derived from the subject. Thus, a patient population for treatment with a Hec1 inhibitor may be selected on the basis of subjects showing insufficient/mutated/deleted p53 (TP53) status.

It should be appreciated that, beyond their utility as individual indicators, Hec1, Rb, and p53 gene status and expression may be used in combination as a basis for selection of a patient population for treatment with a Hec1 inhibitor. For example, Hec1 genotype, Hec1 expression, Rb genotype, Rb expression, p53 genotype, and/or p53 expression may be utilized individually or in any combination as an indicator of sensitivity of neoplastic disease or cell lines to a Hec1 inhibitor compound.

It should be appreciated that detection, quantification, and/or characterization of genes and gene products, such as (for example) genes and gene products related to Hec1, Rb, and p53, may include labeling or tagging of a gene or gene product and/or the formation of a detectable complex. Such labeling can be direct or indirect. For example, a gene or gene product (such as RNA or protein) may directly labeled by modifying its composition so as to render it detectable, for example by affixing a detectable moiety to the gene and/or gene product to be characterized to form a detectable complex. Similarly, a gene or gene product may be indirectly labeled by interacting with a binding partner (such as, for example, a complementary nucleic acid sequence, complementary nucleic acid analog sequence, aptamer, or antibody) that carries a detectable moiety to form a detectable complex. Alternatively, a gene or gene product (for example, from a patient sample) may be labeled by its ability to displace a gene analog that carries a detectable moiety or a gene product analog that carries a detectable moiety from a binding partner (such as, for example, a complementary nucleic acid sequence, complementary nucleic acid analog sequence, aptamer or antibody) and thereby modulate the formation of a detectable complex. Suitable detectable moieties include, but are not limited to, fluorescent molecules, phosphorescent molecules, luminescent molecules, enzymes, metals, biotin and/or biotin analogs, quantum dots, microparticles, radionuclides, nucleic acids and/or nucleic acid analogs, isotopic mass labels, spin labels, positive or negative charges, or a combination of these.

In this context, it should be noted that all known manners of determination of genotype and/or quantification of Hec1, Rb, and/or p53 nucleic acid and protein products are deemed suitable for use herein. Particularly suitable methods include (but are not limited to) DNA sequencing, copy number determination, haplotype determination, RNA sequencing, qPCR, RT-PCR, q-RT-PCR, digital PCR, Southern and/or Northern hybridization, FISH, microarray analysis, liquid phase hybridization/quantification, amperometric and/or fluorometric quantification, immunometric determination, and/or any method suitable for characterizing a gene and/or a gene product. Alternatively, or additionally, where cytological or histopathological analysis is indicative of a particular status for Hec1, Rb, and/or p53, separate quantitative analysis may be entirely omitted.

With respect to the treatment with a Hec1 inhibitor, it should be appreciated that all known Hec1 inhibitors are deemed suitable for use herein, and that preferred Hec1 inhibitors include those described in WO 2011/115998 and co-pending U.S. provisional application with the Ser. No. 64/564,773. Therefore, and among other contemplated compounds, particularly preferred Hec1 inhibitors include N-(4-(4-isopropoxy-2,6-dimethylphenyl)thiazol-2-yl)isonicotinamide (100951), N-(4-(4-(4-methoxyphenoxy)-2,6-dimethylphenyl)thiazol-2-yl)isonicotinamide (101001), 2-fluoro-N-(4-(4-(4-methoxyphenoxy)-2,6-dimethylphenyl)thiazol-2-yl)isonicotinamide (101015), N-(4-(4-(5-(2-methoxyethoxy)pyrazin-2-yloxy)-2,6-dimethylphenyl)thiazol-2-yl)isonicotinamide (110091), N-(4-(4-(5-(2-methoxyethoxy)pyrazin-2-ylthio)-2,6-dimethylphenyl)thiazol-2-yl)isonicotinamide (110095), and N-(4-(4-(5-(2-(dimethylamino)ethoxy)pyrazin-2-ylthio)-2,6-dimethylphenyl)thiazol-2-yl)isonicotinamide (110096).

It is still further contemplated that the Hec1 inhibitor may be co-administered with one or more cytotoxic agents, for example with an antineoplastic metabolite, a topoisomerase I or II inhibitor, and/or a microtubule active agent. All such known agents are deemed suitable for use herein. With respect to the dosage of such agents, such agents may be administered at the currently known dosages, or somewhat below such known dosages.

Surprisingly, where contemplated Hec1 inhibitors are co-administered with one or more cytotoxic agents, synergistic activity is observed with selected compounds, as further described in more detail below. Most advantageously, synergistic responses may be observed for a combination of Hec1 inhibitor and taxol, doxorubicin, and topotecan. While not limiting to the inventive subject matter, it is contemplated that synergistic action may be observed in cells and/or tissues where the cells and/or tissue are sensitive to Hec1 inhibitors at concentrations equal to or less than 100 nM (Table 9 to Table 11).

Equally remarkable, contemplated Hec1 inhibitor compounds also exhibit significant activity against various cell lines that are considered to be drug resistant, thus providing an additional venue for treatment of otherwise refractory cells and tissues (Table 8). Additionally, the inventors also observed that the Hec1 inhibitors contemplated herein exhibited activity and trigger an apoptotic response(s) in responsive cells (GI50<1 µM), and do not trigger induction of an apoptotic response(s) in non-responsive cells (GI50>1 µM) (FIG. 5).

EXAMPLES

Materials and Methods

Cell culture: A549, MDA-MB231, K562, HCT116 cancer cell lines were provided by Dr. Y. S. Lee (Development Center for Biotechnology, New Taipei City, Taiwan). T47D, ZR-75-1 cell lines were obtained from BCRC (Bioresource Collection and Research Center, Taiwan). Cell lines were maintained initially in suggested medium and adapted to be maintained in medium containing 10% fetal bovine serum, low glucose (1 g/L) Dulbecco's Modified Eagle's (DME) Medium at 37° C. in air containing 5% $CO_2$.

Drug sensitivity: Cell lines were screened for drug sensitivity by treatment with specified drugs 24 hours after seeding in appropriate seeding numbers into 96 well plates containing low glucose DME with 10% FBS. The drug was added to the plate in triplicate wells, and the cells are incubated in drug treated medium for 96 hours before cell viability was determined by MTS assay using CellTiter 96® Aqueous non-radioactive cell proliferation assay system (Promega, Madison, Wis. 53711 USA). The MTS assay was performed according to the manufacturer's instructions. Optical density was measured using a Bio-Tek 340 spectrophotometer (Bio-Tek, Winooski, Vt. 05404) and optical readings were then processed in Excel (Microsoft, Redmond, Wash. 98052-7329) and GraphPad Prism 5 linear regression software (GraphPad Software, La Jolla, Calif. 92037 USA) to determine concentration-response curves for calculating relative GI50s. GI50 value refers to a concentration that causes 50% growth inhibition. The % growth inhibition of the test drug on cells were calculated as: [1−(Test Value)/(Control Value)]×100; these values were used to plot concentration-response curves, and then analyzed with linear regression software.

Synergy: GI50s for selected drugs were determined and used to calculate a concentration ratio for use synergy assays with Hec1 inhibitors. Cells were treated with drugs 24 hours after being seeded in appropriate seeding numbers into 96 well plates containing low glucose DME with 10% FBS. Hec1 inhibitor and select drugs were added to the plate in triplicate wells in the determined GI50 concentration ratios, and the cells were incubated in drug treated medium for 96 hours prior to determination of cell viability. Cell viability was determined by MTS assay using a CellTiter 96® Aqueous non-radioactive cell proliferation assay system (Promega, Madison, Wis. 53711 USA) according to the manufacturer's instructions. Optical density was determined using a Bio-Tek 340 spectrophotometer (Bio-Tek, Winooski, Vt. 05404) and were then processed using Excel (Microsoft, Redmond, Wash. 98052-7329) and GraphPad Prism 5 linear regression software (GraphPad Software, La Jolla, Calif. 92037 USA) to determine concentration-response curves for calculating relative GI50s. Synergy was determined by calculating a combination index value using the formula CI (combination index)=(CA,X/ICx,A)+(CB,X/ICx,B), where CA,X and CB,X are the concentrations of drug A and drug B used in combination to achieve x % drug effect. ICx,A and ICx,B are the concentrations for single agents to achieve the same effect.

Gene silencing: Cells were plated into the wells of 96 well plates in appropriate cell numbers and transfected by the siPort NeoFx transfection method (Life Technologies, Carlsbad, Calif. 92008 USA) according to manufacturer instructions, maintained for 24 hours, then treated with drug. Cells were incubated in drug treated medium for 48 hours then analyzed by MTS assay. Control siRNA Life Technologies, Carlsbad, Calif. 92008; Cell Signaling Technology, Danvers, Mass. 01923 USA; and Santa Cruz Biotechnology, Santa Cruz, Calif. 95060 USA), Rb siRNA (#1: Life Technologies, Carlsbad, Calif. 92008 USA; #2: Santa Cruz Biotechnology, Santa Cruz, Calif. 95060 USA) and p53 siRNA (#1: Cell Signaling Technology, Danvers, Mass. 01923 USA; #2: Cell Signaling Technology, Danvers, Mass. 01923 USA) were used. Cells were treated with drugs 24 hours after seeding and incubated with the drugs for 48 hours before MTS assay. The MTS assay was performed according to the manufacturer's instructions (Promega, Madison, Wis. 53711 USA).

Immunoblots: Cell lysates were by incubation of cells in radioimmunoprecipitation assay (RIPA) buffer (50 mM Tris-HCl, pH7.4, 150 mM NaCl, 1% NP40, 0.25% DOC, 0.1% SDS, 1 mM NaVO4, 1 mM EDTA, 1 ug/ml leupeptin, 1 µg/ml pepstatin) or 2.5× sample buffer (50 mM Tris-HCl, pH6.8, 1% SDS, 2.5% BME, 7.5% Glycerol, Bromophenol blue). Tissue samples were immersed in RIPA buffer, disrupted with a homogenizer, and centrifuged to clarify. Samples were then subjected to SDS-PAGE, blotted onto immunoblotting membranes, and incubated with primary antibodies in 3% BSA-TBST. Horseradish peroxidase— conjugated secondary antibodies were used for protein detection by enhanced chemiluminescence (Millipore, Billerica, Mass. 01821 USA). The following antibodies were used for Western blotting: anti-Rb monoclonal antibody 1F8 (Abcam, Cambridge, Mass. 02139-1517 USA); anti-p53 monoclonal antibody (Santa Cruz Biotechnology, Santa Cruz, Calif. 95060 USA); anti-β-actin monoclonal antibody AC-15 (Sigma Aldrich, St. Louis, Mo., USA).

Real-time Quantitative PCR: Total RNA was isolated using a Quick-RNA miniPrep kit (Zymo Research, Irvine, Calif. 92614 USA). Reverse transcription and quantitative real-time PCR was performed on an ABI Prism 7500 (Life Technologies, Carlsbad, Calif. 92008 USA) using a One Step SYBR ExTaq qRT-PCR kit (Takara-Bio, Shiga, Japan) following manufacturer's instructions. Primer sequences used for GAPDH were: 5'-GGTTTACATGTTCCAATAT-GATTCCA-3' (forward), 5'-ATGGGATTTCCATTGAT-GACAAG-3'(reverse). Primers sequences used for Rb were: 5'-GCAGTATGCTTCCACCAGGC-3'(forward), 5'-AAGGGCTTCGAGGAATGTGAG-3'(reverse). Primers sequences used for p53 were: 5'-GCCCCCAGGGAG-CACTA-3'(forward), 5'-GGGAGAGGAGCTGGTGTTG-3' (reverse).

Gene expression in clinical samples: HEC gene expression data were obtained from the GSE database, analyzed and expressed as the logarithm of gene expression intensity in base 2.

The following discussion provides numerous exemplary embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Moreover, unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Correlation between Hec1 expression and cellular sensitivity to Hec1 inhibitors: Results of characterizing a variety of cancer cell lines for their sensitivity to Hec1 inhibitors are shown in Table 1. As is readily apparent, such cells vary in their sensitivities to Hec1 inhibitor. Here, the cell lines as indicated were treated with Hec1 inhibitor (101001) and analyzed for their proliferative and metabolic activity. Table 1 the lists screened cell lines in order of increasing GI50, and groups them according to their sensitivity to Hec1 inhibitor.

TABLE 1

| Sensitivity | Cell Lines | Cancer Type | pRb | p53 | TAI-101001 GI50 (nM) |
|---|---|---|---|---|---|
| Strong sensitivity ($GI_{50} < 50$ nM) | K562 | chronic mycloid leukemia | WT | mut | 13.48 |
| | HeLa | cervical cancer | mut | inactivated | 15.83 |
| | T47D | breast, metastatic-pleural, invasive ductal carcinoma | W | mut | 17.09 |
| | U-937 | acute mycloid leukemia | WT | null | 22.03 |
| | MDA-MB-453 | breast, metastatic-effusion, adenocarcinoma | WT | mut | 23.57 |
| | RPMI8226 | acute mycloid leukemia | mut | mut | 27.19 |
| | KG-1 | myeologenous leukemia | rearranged | reduced/no | 28.90 |
| | MDA-MB-468 | breast, metastatic-pleural, invasive ductal carcinoma | mut/no | mut | 33.64 |
| | HCT116 | colorectal carcinoma | low | WT | 38.94 |
| | COLO205 | colorectal carcinoma | WT | no | 40.23 |
| | MDA-MB-231 | breast, metastatic-pleural, invasive ductal carcinoma | WT | mut | 43.31 |
| Moderate sensitivity (50 nM < $GI_{50}$ < 100 nM) | PC3 | prostate cancer | WT | null | 60.00 |
| | MCF7 | breast, metastatic, pleural, invasive ductal carcinoma | WT | heterogenous WT | 63.70 |
| | NCI-H520 | non-small cell lung cancer | WT | reduced mRNA | 67.86 |
| | ZR-75-30 | breast, metastatic-ascites, invasive ductal carcinoma | WT | WT | 76.78 |
| | ZR-75-1 | breast, metastatic-ascites, invasive ductal carcinoma | WT | WT | 79.62 |
| | Huh7 | hepatocellular carcinoma | WT | mut | 84.32 |
| | BT474 | breast, primary, invasive ductal carcinoma | WT | mut | 85.70 |
| | PLC/PRF/5 | hepatocellular carcinoma | WT | inactivated | 91.61 |
| | Hep3B | hepatocellular carcinoma | no | deletion | 96.06 |
| Low sensitivity (100 nM < $GI_{50}$ < 1μM) | U2OS | osteosarcoma | Less active | WT | 139.30 |
| | Hs578T | breast, metastatic, invasive ductal carcinoma | WT | mut | 143.03 |
| | MV4-11 | acute mycloid leukemia | WT | mut | 231.00 |
| | RS4:11 | acute mycloid leukemia | WT | mut | 254.00 |
| | HepG2 | hepatocellular carcinoma | WT | WT | 272.67 |
| | MOLM-13 | acute mycloid leukemia | WT | mut | 315.00 |

TABLE 1-continued

| | Cell Lines | Cancer Type | pRb | p53 | TAI-101001 GI50 (nM) |
|---|---|---|---|---|---|
| Resistant (GI50 > 1 μM) | A549 | non-small cell lung cancer | WT | WT | >10 μM |
| | HCC1954 | breast, invasive ductal carinoma | mut | WT | >10 μM |
| | MDA-MB-361 | breast, metastatic-brain, adenocarcinoma | WT | no | >10 μM |
| | MOLT-4 | acute lymphoblastic leukemia | WT | WT | >30 μM |
| | N87 | gastric cancer | WT | WT | >30 μM |

Figures 1, 1D:
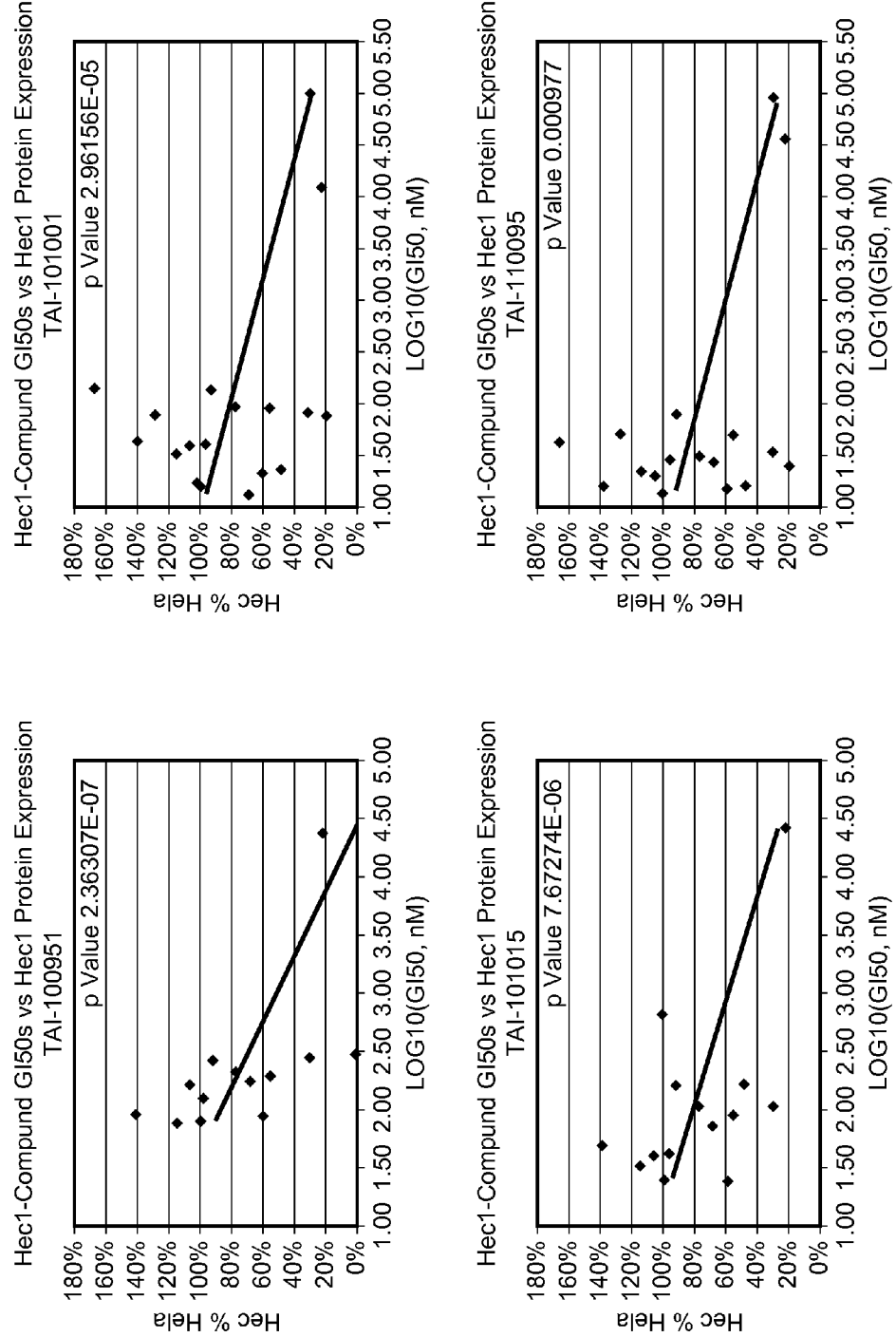
FIG. 1 shows the relationship between the GI50s of Hec1 inhibitory compounds and Hec1 expression.
FIG. 1D shows the log 10 of GI50 data collected from cell line screening assays utilizing four Hec1 compound analogues (100951, 101001, 101015, and 110095) plotted against Hec1 protein expression levels. A 2-tailed T test was utilized to determine significance (P-value for all drugs tested was $4.3 \times 10^{-17}$).

To characterize possible mechanisms for drug resistance in Hec1 inhibitor resistant cell lines, expression levels of Hec1 protein and RNA in Hec1 inhibitor 101001 sensitive and resistant cell lines were determined. Similar studies were performed to characterize expression levels of Hec1 protein in cell lines identified as sensitive (GI50<300 nM) and resistant (GI5->300 nM) to a second Hec1 inhibitor, 110095. Asynchronously maintained cell lines were lysed and their total protein immunoblotted for expression levels of Hec1. Hec1 protein expression levels were quantitated and expressed in % relative to HeLa expression levels (FIG. 1A). Similarly, asynchronously maintained cell lines were collected and their total RNA analyzed for expression levels of Hec1 relative to HeLa by quantitative real time PCR (FIG. 1B). Hec 1 inhibitor 101001 resistant cell lines (GI50>10 uM) A549 and MDA-MB-361 were noted to have low Hec1 expression levels while 7 out of 9 very sensitive cell lines (GI50<50 nM) had Hec1 levels higher than K562, the cell line with the lowest GI50. Similarly, cell lines sensitive to Hec1 inhibitor 110095 showed a statistically significant (p value<0.0001) elevation of Hec1 protein expression relative to resistant cell lines (FIG. 1C). FIG. 1D shows similar results from studies with four different Hec1 inhibitors. The log of GI50 data collected from cell line screening assays from four Hec1 compound analogues (100951, 101001, 101015, and 110095) were plotted against quantitated Hec1 protein expression levels and a 2-tailed t test utilized to determine significance in P values. A P-value of $4.32914 \times 10^{-17}$ was found, strongly implying that Hec1 expression levels may be used effectively as a biomarker in designs for clinical trials for a Hec1 inhibitor. Overall, expression of Hec1 showed a positive correlation to cellular sensitivity to Hec1 inhibitors. Additional studies in HeLa cells showed that the relationship between Hec1 protein and RNA expression (as a function of total protein and total RNA, respectively), as shown in FIG. 1E, is approximately linear. This suggests that, advantageously, either Hec1 protein expression or Hec1 RNA expression may be utilized effectively as a biomarker in designs for clinical trial for a Hec1 inhibitor.

Figure 2B:
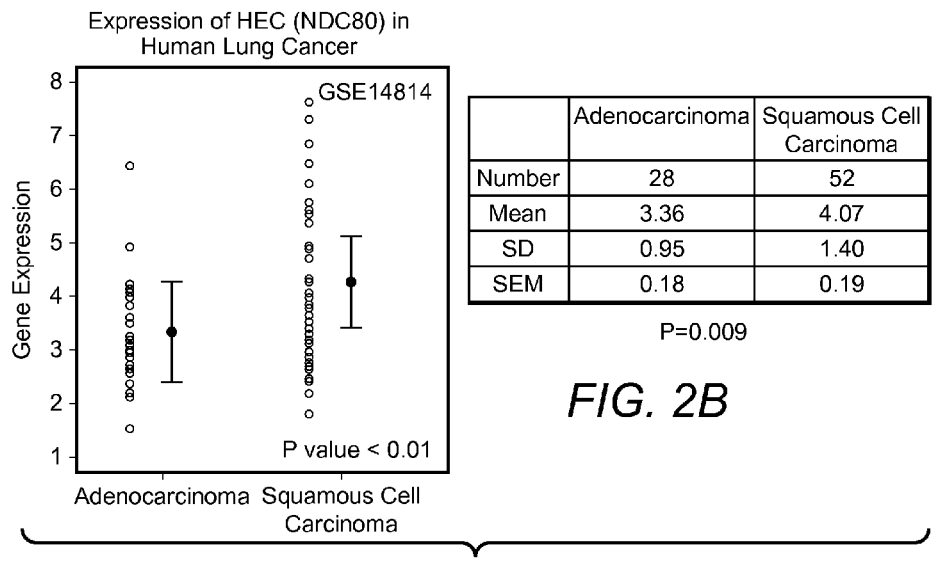
Figure 2C:
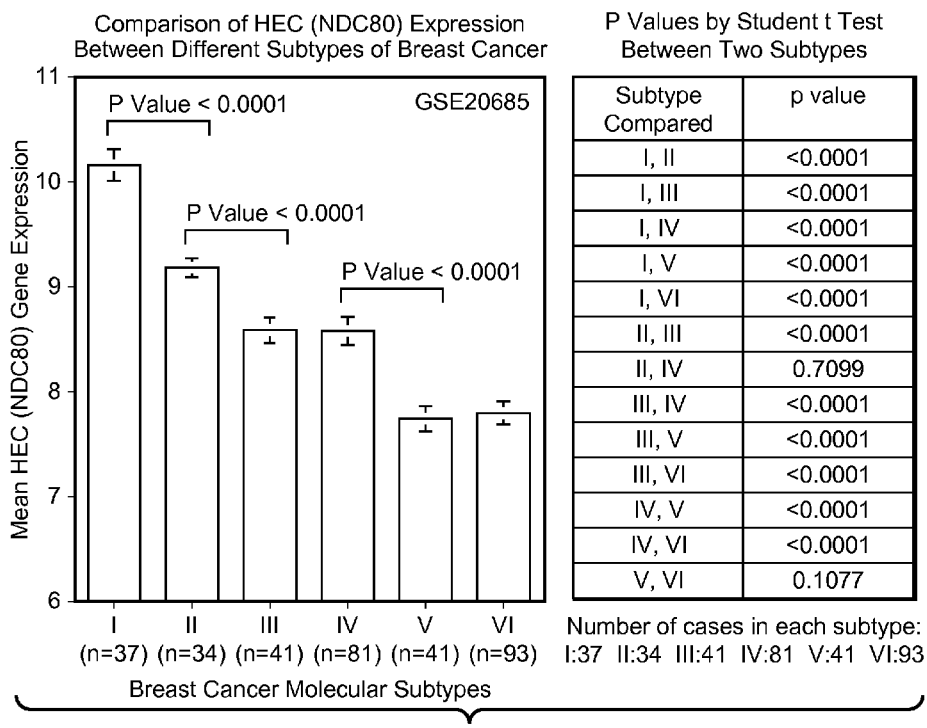
FIG. 2C shows Hec1(NDC80) expression data obtained from GEO database GSE 20685 for breast cancer tumor samples expressed as the logarithm of expression intensity; results show high Hec1 expression in type I.

Hec1 expression in clinical cancer sample types and subtypes: Genome-wide expression profiles show that Hec1 is up-regulated in breast, lung, liver and brain cells and that Hec1 expression correlates with tumor grade and prognosis. Clinical cancer patient tissue samples were collected and analyzed for their Hec1 expression levels. Data reveals significantly higher Hec1 expression levels in certain cancer types and subtypes. FIG. 2A and FIG. 2B depict HEC (NDC80) expression data obtained from GEO databases GSE8894 (FIG. 2A) and GSE14814 (FIG. 2B) for lung cancer tumor samples representing adenocarcinoma and squamous cell carcinoma, analyzed and expressed as base 2 logarithms of expression intensity relative to normal tissue. In both datasets, the mean expression of HEC(NDC80) gene is elevated in squamous cell carcinoma cells. A similar elevation of Hec1 expression was found in colon cancer cells (not shown). Similarly, HEC(NDC80) expression data was obtained from GEO database GSE 20685 for breast cancer tumor samples of various molecular subtypes, analyzed, and expressed as base 2 logarithms of expression intensity relative to normal tissue. HEC is overexpressed in breast cancer molecular subtype I, as shown in its gene expression profile (FIG. 2C). Expression of Hec1 protein in breast cancer tumor samples isolated from patients was also characterized, as was the molecular subtype of the breast cancer, and summarized in Table 2. Molecular subtype I and IV show elevated Hec1 protein expression. Properties of different classified breast cancer molecular subtypes are also listed in Table 1, which shows retinoblastoma (Rb) and p53 gene and protein status in screened cell lines and lists cell lines in order of increasing GI50. These results strongly indicate that type and/or the molecular subtype of a tumor or tumor cell line may be a critical indicator for proper patient selection during clinical trials for Hec1 inhibitor.

TABLE 2

| Breast Cancer Molecular Subtype | Hec1 | p84 | actin |
|---|---|---|---|
| I | ++ | +++++ | +++++ |
| I | + | +++ | +++ |
| I | - | ++ | + |
| II | - | - | - |
| II | - | ++ | +++++ |
| II | - | ++++ | ++ |
| III | - | + | ++++ |
| III | - | ++ | +++++ |
| III | - | +++ | +++++ |
| IV | + | +++ | +++++ |
| IV | + | ++ | +++++ |
| V | - | - | - |
| V | - | + | + |
| V | - | ++++ | +++ |
| VI | - | + | + |
| VI | - | - | - |
| VI | - | - | - |

Correlation of Rb and p53 status with cellular sensitivity to Hec1 inhibitors: Hec1 was discovered through its interaction with the retinoblastoma protein Rb. This suggests that there may be a relationship between the Rb status of cancer cell lines in the present drug screening system (Table 1) and sensitivity to Hec1 inhibitor. Surprisingly, the pattern of Rb and p53 status in the present cell lines may indicate a requirement for the presence of a mutated form of Rb and/or a mutated form of p53. As shown in Table 3, mutated/aberrant Rb as a single biomarker is less significant than mutated/aberrant p53, with P values of 0.3 and <0.005, respectively.

TABLE 3

| Hec1 expression | | | |
|---|---|---|---|
| | Total | High | Low |
| Sensitive | 17 | 16 | 1 |
| Resistant | 2 | 0 | 2 |
| P value < 0.01 | | | |

| P53 expression | | | Hec1 +/- P53 expression | | | |
|---|---|---|---|---|---|---|
| | Total | mutant | wild-type | | Total | High | Low |
| Sensitive | 25 | 22 | 3 | Sensitive | 25 | 25 | 0 |
| Resistant | 5 | 1 | 4 | Resistant | 5 | 1 | 4 |
| P value < 0.005 | | | | P value < 0.0001 | | | |

| Rb expression | | | | Hec1 +/- Rb expression | | | |
|---|---|---|---|---|---|---|---|
| | Total | mutant | wild-type | | Total | mutant | wild-type |
| Sensitive | 25 | 7 | 18 | Sensitive | 25 | 18 | 7 |
| Resistant | 5 | 0 | 5 | Resistant | 5 | 0 | 5 |
| P value = 0.3 | | | | P value < 0.005 | | | |

| Rb +/- p53 expression | | | | Hec1 +/- Rb +/- p53 expression | | | |
|---|---|---|---|---|---|---|---|
| | Total | High | Low | | Total | mutant | wild-type |
| Sensitive | 25 | 23 | 2 | Sensitive | 25 | 25 | 0 |
| Resistant | 5 | 1 | 4 | Resistant | 5 | 1 | 4 |
| P value < 0.005 | | | | P value < 0.0001 | | | |

Similar results are shown in Table 4, where mutant Rb as a single biomarker has a P value of >0.6, whereas mutant p53 has a P value of <0.007.

TABLE 4

| | High Heel/+ Mutant p53/+ Mutant Rb | Mutant p53/+ mutant Rb | Mutant Rb | Mutant p53 | High Hec1 |
|---|---|---|---|---|---|
| Total | 31 | 31 | 30 | 30 | 18 |
| Sensitive Mutants | 23 | 22 | 7 | 20 | 14 |
| Sensitive Nonmutants | 1 | 2 | 17 | 3 | 2 |
| Insensitive Mutants | 2 | 2 | 0 | 2 | 0 |
| Insensitive Nonmutants | 5 | 5 | 5 | 5 | 2 |
| 101001 sensitivity cutoff | 270 nM | 270 nM | 270 nM | 270 nM | 270 nM |
| P value | 0.000694 | 0.00268 | 0.6550545 | 0.006661 | 0.039216 |

Figure 3B:
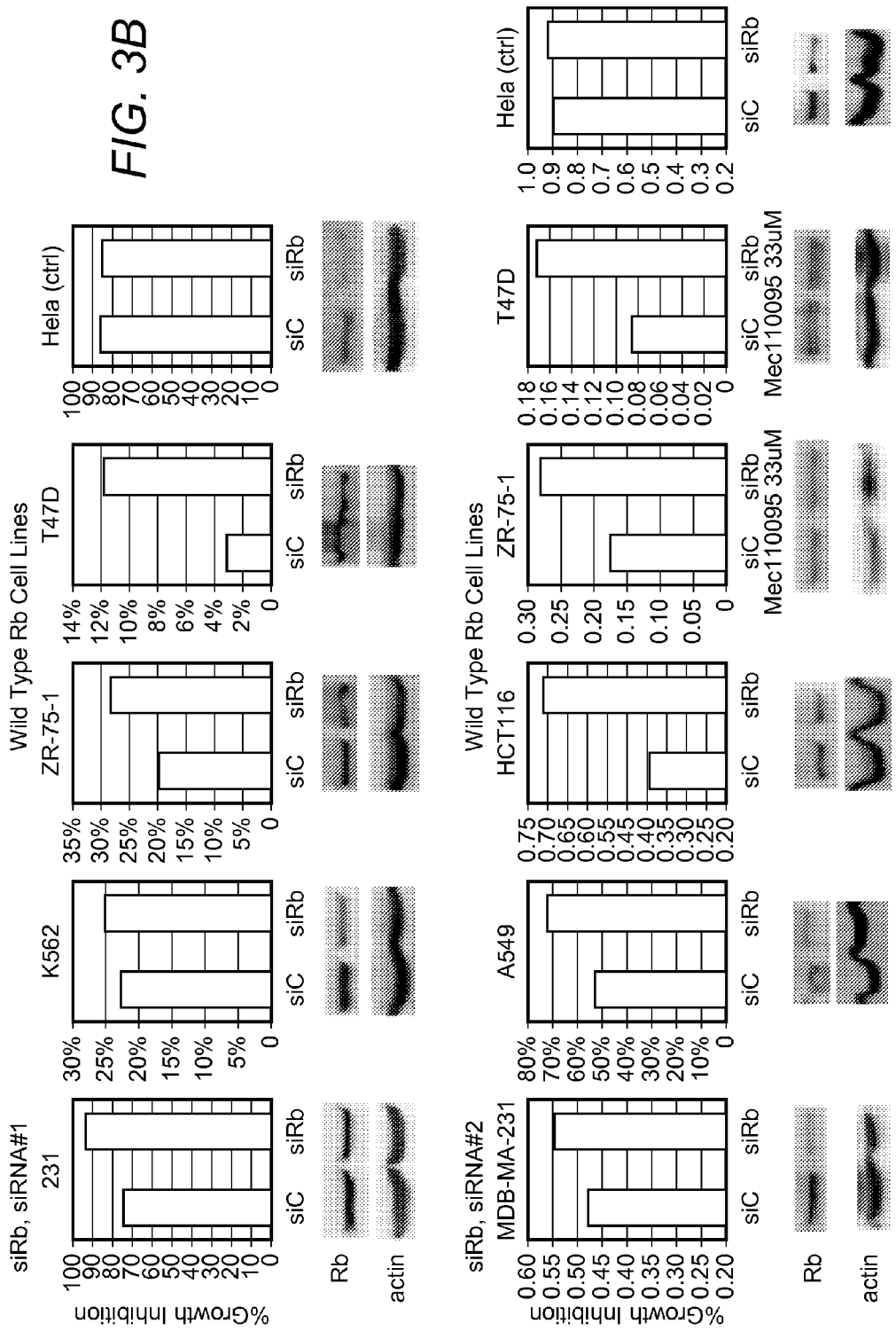
FIG. 3B shows cellular sensitivity of selected cell lines with wild type Rb (231, MDA-MB-231, K562, ZR-75-1, T47D, A549, HCT116) or mutated Rb (HeLa) transfected with one of two siRNAs directed to Rb and treated as in FIG. 3A, expressed as percent growth inhibition relative to non-drug-treated cells. Immunoblots of lysates from transfected cells probed for Rb are shown below the corresponding inhibition graphs.

To further clarify the role of these tumor suppressors in cellular sensitivity to Hec1 inhibitor, siRNA was used to selectively knockdown or reduce expression of Rb and p53 in select cell lines and the effect on their sensitivity to Hec1 inhibitor was characterized. Surprisingly, Rb knockdown induced an increase in Hec1 inhibitor sensitivity in several cancer cells lines carrying wild type Rb (MDA-MB-231, K562, ZR-75-1, T47D, HCT116), but had no effect in cell lines with mutated Rb (HeLa) (FIGS. 3A-3B). FIG. 3A shows results of viability studies of wild-type Rb MDA-MB-231 cells transfected with siRNA directed to Rb (siRb) and control siRNA, then treated with the Hec1 inhibitor 101001; cellular sensitivity is expressed in GI50(μM). Results of quantitation of Rb RNA from transfected cells by real time PCR are also shown, and show a significant drop in Rb RNA in siRNA treated cells. FIG. 3B shows results of siRb transfection of selected cell lines with wild type Rb (MDA-MB-231, K562, ZR-75-1, T47D, A549, HCT116) or mutated Rb (HeLa) and treated as in FIG. 3A; cellular sensitivity is expressed as percent growth inhibition relative to non-drug-treated cells. Cell lysates from transfected cells were collected and analyzed for Rb protein by immunoblotting; blots are shown below the corresponding inhibition graphs. Actin was included as a loading control.

Figure 4B:
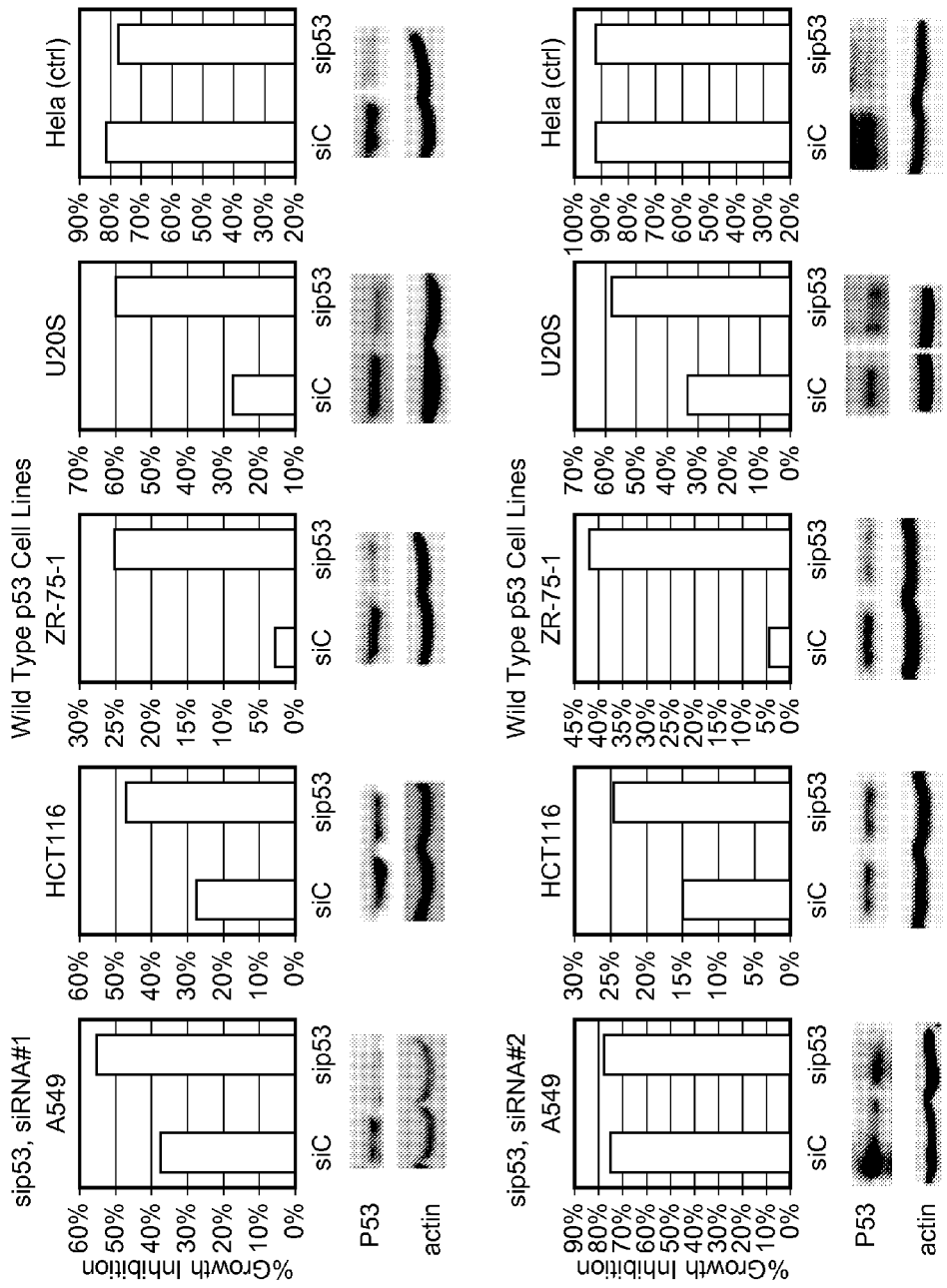
FIG. 4B shows cellular sensitivity of selected cell lines with wild type p53 (A549, HCT116, ZR-75-1, U2OS) or mutated p53

Silencing of p53 induced similar sensitizing effects in cells carrying wild type p53 (A549, HCT116, ZR-75-1, U205), but surprisingly had no effect on cells carrying mutated p53 (MDA-MB-231, HeLa) as shown in FIGS. 4A-4B. FIG. 4A shows results from wild-type p53 cells (A549, HCT116) and mutant (MDA-MB-231) transfected with siRNA directed to p53 (sip53) and then treated with Hec1 inhibitory compound 101001. Cells were analyzed for viability and cellular sensitivity expressed in GI50 (nM). RNA from transfected cells were also analyzed for p53 RNA level by quantitative real time PCR. Increased sensitivity of sip53 treated cells are shown by the decreased GI50 of sip53 treated cells with wild-type p53, which was not observed in cells with mutated p53. Similarly, FIG. 4B shows the results of transfection of selected cell lines with wild type p53 (A549, HCT116, ZR-75-1, U205) or mutated p53 (HeLa) with siRNA directed to p53 and treated as in FIG. 4A. Cellular sensitivity is expressed as percent growth inhibition relative to non-drug-treated cells. Results of immunoblots of cell lysates from transfected cells for p53; corresponding blots are shown below the corresponding inhibition graphs. Overall, these results suggest that cancer cells with impaired Rb and p53 are more sensitive to Hec1 inhibitors through an as yet unknown pathway, which may provide additional biomarkers useful for guidance of patient selection for clinical Hec1 inhibitor therapy.

It should, therefore, be appreciated that three biomarkers for the selection of sensitive cell lines and clinical patients for sensitivity to Hec1 inhibitors are presented according to the inventive subject matter. Increased expression of Hec1, mutated Rb and/or mutated p53 are indicators of tumors and cell lines that are potentially susceptible to Hec1 inhibitors. These factors may be predictive individually or in any combination. Surprisingly, the combined P value for all three biomarkers is <0.0001 (Table 3). These provide a selection guide for the design of clinical studies to select for patients that are more likely responsive to Hec1 inhibitor therapy.

Effectiveness of Hec1 inhibitors relative to current cytotoxic drugs: The sensitivity of tumor derived cells to Hec1 inhibitor and a selection of cytotoxic drugs currently used in cancer treatment (in terms of GI50) are shown in Tables 5-7. Table 5 summarizes the GI50s of a number of breast cancer derived cell lines to Hec1 inhibitor 101001 and several cytotoxic drugs (paclitaxel, doxorubicin, topotecan, and sorafenib). Table 6 shows similar data for a number of liver cancer cell derived cell lines. Similarly, Table 7 summarizes the GI50s of other cancer-derived cell lines to Hec1 inhibitor 101001 and paclitaxel, doxorubicin, and topotecan. For the most part Hec1 inhibitors were more potent (i.e. had a lower GI50) than select cytotoxic agents in select cell lines. Surprisingly, Hec1 inhibitors were also effective on several drug resistant cell lines, including taxol-resistant cell lines Mex-SA/Dx5 and NCI/ADR-Res and Gleevec-resistant cell line K562R, as shown in Table 8. These results provide a basis for the use of Hec1 inhibitor as an alternative to or in combination with therapeutic regimens with cytotoxic drugs such as, for example, taxol, doxorubicin, topotecan and Gleevec.

TABLE 5

| Breast Cancer Cell Lines | GI50 (nM) | | | | |
| --- | --- | --- | --- | --- | --- |
| | 1011101 | paclitaxel | doxo-rubicin | topotecan | sorafenib |
| MDA-MB-231 | 43.31 | 3.00 | 213.80 | 346.73 | 3044.00 |
| MDA-MB-468 | 33.64 | 2.38 | 28.27 | 10.71 | 3171.67 |
| MDA-MB-453 | 23.57 | 1.42 | 158.04 | 92.34 | 2521.00 |
| T47D | 17.09 | 3.19 | 11.94 | 9.43 | 1730.00 |
| ZR-75-1 | 79.62 | >10 µM | 92.88 | 36.32 | 4337.00 |
| ZR-75-30 | 76.78 | N.D. | N.D. | N.D. | N.D. |
| Hs578T | 143.03 | 8.39 | 711.30 | 4955.00 | N.D. |

TABLE 6

| Liver Cancer Cell Lines | GI50 (nM) | | | | |
| --- | --- | --- | --- | --- | --- |
| | 101001 | paclitaxel | doxorubicin | topotecan | sorafenib |
| Huh-7 | 84.32 | 93.53 | 182.80 | 50.91 | 4501.00 |
| PLC/PRF/5 | 91.61 | 8.58 | 69.72 | 174.40 | 3762.00 |
| HepG2 | 272.67 | >50 µM | 746.30 | 434.90 | 8254.00 |
| Hep3B | 96.06 | 9.47 | 247.70 | 422.40 | 3676.00 |

TABLE 7

| Other Cancer Cell Lines | GI50 (nM) | | | | |
| --- | --- | --- | --- | --- | --- |
| | 101001 | paclitaxel | doxorubicin | topotecan | sorafenib |
| K562 | 13.48 | 3.46 | 36.22 | 36.12 | N.D. |
| HeLa | 15.83 | 7.80 | 242.00 | 636.55 | N.D. |
| HCT116 | 38.94 | N.D. | N.D. | N.D. | N.D. |
| COLO205 | 40.23 | N.D. | N.D. | N.D. | N.D. |
| U2OS | 139.30 | N.D. | N.D. | N.D. | N.D. |
| U-937 | 22.03 | N.D. | N.D. | N.D. | N.D. |

TABLE 8

| Cell Line | Origin | 101001 GI50 (nM) | 110095 GI50 (nM) | 100951 GI50 (nM) | 101015 GI50 (nM) | Paclitaxel GI50 (nM) |
| --- | --- | --- | --- | --- | --- | --- |
| MEX-SA/Dx5 | Multi-drug resistant uterine sarcoma | 34.89 | 7.27 | 75.29 | 34.89 | 6247 |
| NCI/ADR-RES | Multi-drug resistant uterine sarcoma | 28.55 | 19.46 | 52.58 | 21.65 | 2329 |
| K562R | Gleevec resistant myelogenous leukemia | 29.57 | 10.44 | 74.44 | 26.01 | 34.45 |

Synergistic effects of Hec1 inhibitor with cytotoxic drugs: Combination therapy is a promising approach to more effective treatment of cancer patients. Drugs that can target pathways unreached by other current anti-cancer drugs have even better clinical potential to be incorporated into current therapeutic regimens. As noted above, results of single drug studies strongly suggest that Hec1 inhibitors may be effective in such combination therapies. To investigate possible clinical combination therapeutic approaches for Hec1 inhibitors, synergistic effects of Hec1 inhibitors with several currently available cytotoxic agents used in cancer therapy were characterized. Hec1 inhibitor-responsive cancer cells used for screening were treated with a mixture of Hec1 inhibitor and select anti-cancer drug at appropriate concentration ratios and evaluated for cell viability. A combination index (CI) was calculated from the GI50s obtained as described above to represent additive (CI=about 1), synergistic (CI<1), or antagonistic (CI>1) effects. Table 9 summarizes the results of synergism studies on a number of cancer derived cell lines treated with Hec1 inhibitor 110001 in combination cytotoxic drugs. Table 10 summarizes results from a similar study performed using Hec1 inhibitor 110095. Similarly, Table 11 summarizes combination index (CI) values obtained for Hec1 inhibitors 100951(0951), 101001(1001), 101015(1015), and 110095(0095) and cytotoxic drugs for leukemia, cervical cancer, breast cancer, and liver cancer cell lines. Significant synergistic effects of Hec1 inhibitors (i.e. CI<1) were identified with taxol, doxorubicin, and topotecan in many of the cell lines tested. This suggests that Hec1 inhibitors may provide an additional therapeutic modality for treatment of neoplastic disease or inhibition of the growth of cancer cell lines when added to current cytotoxic drug regimes.

Mechanism of Hec1 inhibitor induced cell death: P53 is known as an important regulator of the cell cycle in G1 and G2 phases, and controls apoptosis in response to aberrant proliferative signals and stress. Since most of the Hec1-inhibitor sensitive cell lines the inventors have discovered have mutant p53, it could be speculated that p53-independent apoptotic pathways may be involved in Hec1 inhibitor induced cell death. P73 is a member of the p53-family that mediates apoptosis and replaces p53 function in p53-deficient cells. P73 is therefore a potential candidate for a molecule that mediates apoptosis leading to Hec1 inhibitor induced cell death. To investigate this, drug-responsive (HeLa) and drug-resistant cells (A549) carrying mutant p53 proteins were treated with Hec1 inhibitor 110095 for varying lengths of time. Results of immunoblots for phosphorylated p73 show that Hec1 inhibitors induced time-dependent phosphorylation of p73 in treated cells, peaking at 48 hours after drug treatment (FIG. 5A). Such phosphorylation suggests that Hec1 inhibitors may act to induce cell death, at least in part, by modulating p73 activity.

Similarly, HeLa (FIG. 5B) cells were treated for 24 or 48 hours with select Hec1 inhibitors 110091 (91), 110093 (93), 110095 (95), at 1 μM and lysates immunoblotted for apoptotic markers caspase3 and PARP and anti-apoptotic markers Mcl-1, XIAP, and Bcl-2. Actin is shown as a loading control. A549 cells were similarly treated with Hec1 inhibitors 100951(0951), 101001(1001), 101015(1015), 110078 (0078), and 110079(0079), and the results summarized in FIG. 5C. Similar studies utilizing a different Hec1 inhibitor are shown in FIG. 5D, which illustrates the results of treatment of HeLa and A549 cell lines with Hec1 inhibitor 101001. Hec1 inhibitor treatment led to activation of apoptotic caspases in drug-responsive cells (HeLa) (FIG. 5B, FIG. 5D). Similar treatment of a resistant cell line (A549) did not show a similar response (FIG. 5C, FIG. 5D). This suggests that in mutant p53 cells (HeLa), Hec1 inhibitors are able to induce p73 activation to trigger p73-dependent apoptosis leading to drug induced cell death.

TABLE 9

| Cell line, (Origin) | Cytotoxic drug, (GI50) | 110001 GI50 | Cytotoxic drug:110095 Ratio used | Combination Index | Synergy |
|---|---|---|---|---|---|
| K562 (Leukemia) | doxorubicin, (36.22 nM) | 43.77 nM | 0.83 | 0.66 | Yes |
| MB-468 (breast cancer) | doxorubicin, (27.01 nM) | 33.64 nM | 0.80 | 0.87 | Yes |
| Huh7 (liver cancer) | doxorubicin, (182.80) | 84.32 nM | 2.17 | 0.73 | Yes |
| MB-231 (breast cancer) | topotecan, (346.73 nM) | 43.31 nM | 8.01 | 0.78 | Yes |
| MB-468 (breast cancer) | topotecan, (10.71 nM) | 33.64 nM | 0.32 | 0.74 | Yes |
| Huh7 (liver cancer) | Paclitaxel, (93.53 nM) | 84.32 nM | 1.109 | 0.28 | Yes |
| MB-231 (breast cancer) | paclitaxel, (4.91 nM) | 42.48 nM | 0.116 | 0.68 | Yes |
| K562 (Leukemia) | paclitaxel, (9.93 nM) | 40.65 nM | 0.24 | 0.73 | Yes |
| Huh7 (liver cancer) | sorafenib, (4501 nM) | 84.32 nM | 53.38 | 1.66 | Antagonistic |
| Hep3B (liver cancer) | sorafenib, (3676 nM) | 103.55 nM | 35.50 | 1.50 | Antagonistic |
| Huh7 (liver cancer) | KXO1, (27.16 nM) | 84.32 nM | 0.32 | 1.31 | Additive |

TABLE 10

| Cell line, (Origin) | Cytotoxic drug, (GI50) | 110095 GI50 | Cytotoxic drug:110095 Ratio used | Combination Index | Synergy |
|---|---|---|---|---|---|
| K562 (Leukemia) | doxorubicin, (36.22 nM) | 28.23 nM | 1.28 | 0.49 | Yes |
| MB-468 (breast cancer) | doxorubicin, (27.01 nM) | 21.12 nM | 1.28 | 0.87 | Yes |
| Huh7 (liver cancer) | topotecan, (187.20 nM) | 48.9 nM | 3.74 | 0.76 | Yes |
| MB-231 (breast cancer) | topotecan, (346.73 nM) | 16.48 nM | 21.04 | 0.71 | Yes |
| MB-468 (breast cancer) | topotecan, (10.71 nM) | 21.12 nM | 0.51 | 0.88 | Yes |
| Huh7 (liver cancer) | topotecan, (50.91 nM) | 34.98 nM | 1.46 | 0.75 | Yes |
| Huh7 (liver cancer) | paclitaxel, (30.03 nM) | 34.98 nM | 0.86 | 0.65 | Yes |
| MEX-SA/Dx5 (sarcoma) | paclitaxel, (6247 nM) | 19.46 nM | 321.02 | 1.41 | No |
| NCI/ADR-RES | paclitaxel, (2329 nM) | 10.44 nM | 223.08 | 0.82 | Yes |

TABLE 10-continued

| Cell line, (Origin) | Cytotoxic drug, (GI50) | 110095 GI50 | Cytotoxic drug:110095 Ratio used | Combination Index | Synergy |
|---|---|---|---|---|---|
| (sarcoma) | | | | | |
| K562R (leukemia) | paclitaxel, (34.45 nM) | 7.27 nM | 4.74 | 0.65 | Yes |
| Huh7 (liver cancer) | sorafenib, (4501.00 nM) | 48.9 nM | 92.04 | 1.05 | Additive |
| Huh7 (liver cancer) | KXO1, (27.16 nM) | 48.9 nM | 0.56 | 0.96 | Additive |

Mechanism for differential response to Hec1 inhibitor: Hec1 and Nek2 are cell cycle regulated and are found to reach their highest level of expression during G2/M phase. Since some cell lines are less sensitive to Hec1 inhibitor treatment, differential regulation of such Hec1/Nek2 pathways may be a factor in differential cell responses to Hec1 inhibitors.

TABLE 11

| Origin: Cell Line: | Leukemia K562 | | | | Cervical Cancer HeLa | | | |
|---|---|---|---|---|---|---|---|---|
| Drug: | 0951 | 1001 | 1015 | 0095 | 0951 | 1001 | 1015 | 0095 |
| Taxol | 0.67 | 0.62 | 0.62 | 1.64 | 1.04 | 1.21 | 1.01 | 1.22 |
| Doxorubicin | 0.52 | 0.66 | 0.62 | 0.49 | 3.31 | 4.30 | 6.83 | 1.55 |
| Topotecan | 0.47 | 1.65 | 1.12 | 1.38 | 2.15 | 2.18 | 1.58 | 1.90 |

| Origin: Cell Line: | Breast Cancer MB-231 | | | | Breast Cancer MB-468 | | | |
|---|---|---|---|---|---|---|---|---|
| Drug: | 0951 | 1001 | 1015 | 0095 | 0951 | 1001 | 1015 | 0095 |
| Taxol | 0.51 | 0.68 | 0.98 | 1.21 | 1.36 | 1.01 | 1.16 | 1.08 |
| Doxorubicin | 1.33 | 1.25 | 1.75 | 1.26 | 0.37 | 0.87 | 1.23 | 0.87 |
| Topotecan | 0.75 | 0.78 | 0.85 | 0.71 | 0.84 | 0.74 | 0.74 | 0.88 |

| Origin: Cell Line: | Liver Cancer Huh7 | | | | Liver Cancer PCL/PRF/5 | | | |
|---|---|---|---|---|---|---|---|---|
| Drug: | 0951 | 1001 | 1015 | 0095 | 0951 | 1001 | 1015 | 0095 |
| Taxol | 0.20 | 0.31 | 0.32 | 1.05 | 1.19 | 0.85 | 0.99 | 0.81 |
| Doxorubicin | 0.34 | 0.73 | 0.54 | 0.76 | 1.92 | 1.27 | 1.65 | 2.31 |
| Topotecan | 1.08 | 1.63 | 0.62 | 0.75 | 2.94 | 4.37 | 1.17 | 2.83 |
| KX01 | 0.99 | 1.31 | 1.08 | 1.36 | 1.69 | 2.19 | 1.31 | 1.08 |
| Sorafenib | 0.97 | 1.15 | 1.08 | 0.96 | 0.74 | 0.68 | 1.15 | 1.41 |

| Origin: Cell Line: | Liver Cancer HepG2 | | | | Liver Cancer Hep3B | | | |
|---|---|---|---|---|---|---|---|---|
| Drug: | 0951 | 1001 | 1015 | 0095 | 0951 | 1001 | 1015 | 0095 |
| Taxol | Taxol-resistant IC50 > 10 uM | | | | 1.54 | 1.59 | 2.38 | 2.40 |
| Doxorubicin | 2.58 | 2.13 | 1.74 | 3.00 | 3.99 | 1.71 | 2.00 | 2.27 |
| Topotecan | 1.89 | 2.24 | 1.92 | 3.03 | 1.76 | 1.58 | 1.05 | 1.48 |
| KX01 | 1.71 | 1.70 | 1.68 | 2.32 | 2.14 | 1.86 | 2.32 | 2.79 |
| Sorafenib | 2.15 | 0.78 | 0.89 | 1.88 | 1.45 | 1.24 | 1.91 | 1.20 |

To investigate this possibility, drug-responsive (HeLa, MDA-MB-468, HCT116) and resistant cells (A549) were synchronized by starvation and expression of Hec1 and Nek2 characterized at 1(G1), 27(G27), 32(G32), and 48(G48) hours. Differential expression patterns between Hec1 and Nek2 are apparent, indicating differences in regulation of Hec1/Nek2 pathways (FIG. 6A). Cells were treated with Hec1 compound 110095 at indicated concentration for 48 hours and Nek2 expression characterized by immunoblotting (FIG. 6B). Hec1 inhibitor treatment led to degradation of Nek2 in sensitive cell lines; however this effect is not seen in the resistant cell line (A549) (FIG. 6B). This suggests that Hec1 inhibitor sensitive and Hec1 inhibitor resistant cell lines may regulate (or utilize) Hec/Nek2 pathways differently. In addition, drug-responsive cells (HeLa) were treated with Hec1 inhibitor 110095 (095) for the different time periods and cyclin B1 and cyclin D1 content characterized by immunoblotting (FIG. 6C). Cyclin B1 and cyclin D1 levels were down regulated in drug-responsive cells treated with Hec1 inhibitor. This suggests that cell lines with different cellular context have differential cell cycle pathways that enable select cells to escape Hec1 compound-induced cell death. Identification of characteristic regulatory or cell cycle pathways (for example, characterization of a Hec1/Nek2 pathway and/or cyclin B1 and cyclin D1 regulation) may provide identification of a neoplastic disease and/or cell line that is sensitive to Hec1 inhibitors.

Hec1 expression has also been shown to correlate with tumor grade and prognosis. For example, Hec1 is part of breast cancer prognosis predictor of poor therapeutic outcome, in which the significant prognosis predictors in univariate analysis were Cyclin B1, BUB1, HEC, and the 11-gene signature. This highlights the importance of the use of potent Hec1 small molecular inhibitors in breast cancer patients. Cancer types and subtype may provide a selection guide for the design of clinical studies to select for patients that are more likely responsive to Hec1 inhibitor therapy, as cancer types and subtypes with elevated Hec1 gene expression may be more susceptible to Hec1 inhibitors (as shown by breast cancer molecular subtypes I and IV, above).

Functionally, Hec1 is a component of the mitotic kinetochore that is overexpressed in many cancers and leads to a tumor phenotype. Hec1 expression during the cell cycle is tightly regulated in both normal cells and transformed cells, however kinetochore recruitment of Hec1 is increased in cancer cell lines. As is known, silencing of the retinoblastoma gene (Rb) increased Hec1 mRNA and protein expression. Knockdown of Rb and deregulation of RB/E2F target genes is also known to increase sensitivity to therapeutic doses of DNA-damaging agents in breast cancer cell lines MCF7, T47D and ZR-75-1. Increased aneuploidy and chromosomal instability in RB-defective cancer cells due to increased Hec1 expression may, therefore, contribute to the observed increase in sensitivity to Hec1 inhibitors in cancer cells with mutant Rb genotypes. Genotyping of Rb and/or related genes may provide a selection guide for the design of clinical studies to select for patients and/or cell lines that are likely to be responsive to Hec1 inhibitor therapy.

While the RB and p53 expression profiles and Hec1 inhibitor GI50s of the drug screened cell lines suggest that a mutated RB or mutated p53 is a potentiating factor in Hec1 inhibitor sensitivity, it is not evident that it is the inherent lack of p53 or a gain-of-function of the mutant p53 that sensitizes cells. For example MDA-MB-361 cells do not express p53 proteins, yet were found to be non-responsive to Hec1 inhibitors (i.e. GI50>10 uM). Wild type p53 is a tumor suppressor that protects cells against abnormal proliferation. While early studies mistakenly identified cells with mutant p53 forms and misinterpreted p53 as an oncogene, later research showed that vast overproduction of mutant p53 proteins were hallmarks of cancer and were exacerbated with tumor progression. Overexpression of mutant p53 in such cases resulted in highly tumorigenic cells. Similarly, expression of murine equivalents of human hotspot mutant p53 produced tumors with increased genomic instability, accompanied by aneuploidy, aberrant centrosome amplification, and nonreciprocal chromosome translocations. This suggests that mutated p53 forms may themselves have an active role in the inhibitory mechanism of Hec1 inhibitors. Genotyping of p53 and/or related genes may provide a selection guide for the design of clinical studies to select for patients and/or cell lines that are likely to be responsive to Hec1 inhibitor therapy.

As noted above, presence of mutant p53 is associated with tumor progression, a gain-of-function (GOF) effect. Many GOF effects of mutant p53 are associated with its ability to bind and/or inactivate proteins of the p53 family, such as p63 and p73. P73 can replace p53 genome maintenance functions in p53-deficient cells. As noted above, screening with Hec1 inhibitors to identify sensitive cell lines showed that most sensitive cell lines have mutant p53. This suggests that Hec1 drug induced cell death may occur via one or more p53-independent pathways. It is known that mutant p53 cells have impaired p73/p63-mediated apoptosis. In mutant p53 tumor cells, p73 and p63 are not able to recruit their target genes; the existence of protein complexes of mutant p53, p73 and or p63 can negatively impact the chemosensitivity of cancer cells. The inventors speculate that drug induced cell death in the Hec1 inhibitor context may occur through p73-dependent apoptosis. In this regard, the inventors further speculate that one mechanism in Hec1 inhibitor induced cell death may involve the disruption of one or more interaction(s) between mutant p53 and p73 to promote the activation of p73, leading to p73-dependent apoptosis. Interestingly, treatment of cells with Hec1 inhibitors induced both apoptotic caspase markers and phosphorylation of p73, strongly suggesting activation of a p73-dependent apoptotic pathway. However, the complex functions of p53 may differ in various cellular contexts, and the relationships between Hec1, Hec1 inhibitors, and p53 remain to be fully elucidated. Further compounds, compositions, and experiments are provided in WO 2011/115998, which is incorporated by reference herein.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of diagnosing and treating a patient with a Hec1 inhibitor, comprising:
   a) obtaining a test sample comprising one or more neoplastic cells from the patient;
   b) forming a detectable complex of Hec1 and a detectable complex of p53, wherein Hec1 and p53 are derived from the sample;
   c) utilizing the detectable complex of Hec1 to determine an expression level of Hec1 and utilizing the detectable complex of p53 to determine a mutation status of p53;
   d) comparing the test results from step c to a reference result of Hec1 expression and p53 mutation status from a non neoplastic cell;
   e) detecting an elevated level of Hec1 and mutated or deleted p53 in the test sample as compared to the reference sample;
   f) diagnosing the patient as being susceptible to the Hec1 inhibitor; and
   g) administering a Hec1 inhibitor to the patient, wherein the Hec1 inhibitor is selected from N-(4-(4-isopropoxy-2,6-dimethylpheny)thiazol-2-yl)isonicotinamide (100951), N-(4-(4-(4-methoxyphenoxy)-2,6-dimethylphenyl)thiazol-2-yl)isonicotinamide (101001), 2-fluoro-N-(4-(4-(4-methoxyphenoxy)-2,6-dimethylphenyl)thiazol-2-yl)isonicotinamide (101015), N-(4-(4-(5-(2-methoxyethoxy)pyrazin-2-yloxy)-2,6-dimethylphenyl)thiazol-2-yl)isonicotinamide (Hec110091), N-(4-(4-(5-(2-methoxyethoxy)pyrazin-2-ylthio)-2,6-dimethylphenyl)thiazol-2-yl)isonicotinamide (110095), and N-(4-(4-(5-(2-(dimethylamino)ethoxy)pyrazin-2-ylthio)-2,6-dimethylphenyl)thiazol-2-yl) isonicotinamide, and their salt forms.

2. The method of claim 1 wherein the step of determining the expression level of Hec1 comprises quantification of nucleic acid encoding Hec1.

3. The method of claim 1 wherein the step of determining the expression level of Hec1 comprises sequencing and/or hybridization analysis of a nucleic acid encoding Hec1.

4. The method of claim 1 wherein the step of determining the expression level of Hec1 comprises quantification of Hec1 protein.

5. The method of claim 1 wherein determining the mutation status of p53 comprises quantification of a nucleic acid encoding p53.

6. The method of claim 1 wherein determining the mutation status of p53 comprising sequencing and/or hybridization analysis of a nucleic acid encoding p53.

7. The method of claim 1 wherein the step of determining the mutation status of p53 comprises quantification of p53 protein.

8. The method of claim 1, wherein the neoplastic cell or cells is from breast cancer, lung cancer, colon cancer, or liver cancer.

* * * * *